[12] United States Patent
Laal

(10) Patent No.: US 10,883,989 B2
(45) Date of Patent: Jan. 5, 2021

(54) **PEPTIDES OF *M. TUBERCULOSIS* FOR A SCREENING TEST FOR HIV POSITIVE PATIENTS AT HIGH-RISK FOR TUBERCULOSIS**

(71) Applicant: New York University, New York, NY (US)

(72) Inventor: Suman Laal, Cortland Manor, NY (US)

(73) Assignee: New York University, New York, NY (US)

( * ) Notice: Subject to any disclaimer, the term of this patent is extended or adjusted under 35 U.S.C. 154(b) by 67 days.

(21) Appl. No.: 15/564,086

(22) PCT Filed: Apr. 4, 2016

(86) PCT No.: PCT/US2016/025894
§ 371 (c)(1),
(2) Date: Oct. 3, 2017

(87) PCT Pub. No.: WO2016/161435
PCT Pub. Date: Oct. 6, 2016

(65) Prior Publication Data
US 2018/0136207 A1    May 17, 2018

Related U.S. Application Data

(60) Provisional application No. 62/142,774, filed on Apr. 3, 2015.

(51) Int. Cl.
*G01N 33/569*    (2006.01)

(52) U.S. Cl.
CPC ..... *G01N 33/5695* (2013.01); *G01N 2333/35* (2013.01); *G01N 2469/10* (2013.01); *G01N 2800/26* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 6,245,331 B1 * | 6/2001 | Laal | C07K 16/1289 424/130.1 |
| 6,506,384 B1 * | 1/2003 | Laal | C07K 16/1289 424/130.1 |
| 7,807,182 B2 * | 10/2010 | Laal | C07K 14/36 424/130.1 |
| 8,658,350 B2 * | 2/2014 | Lewinsohn | G01N 33/5695 435/4 |
| 2005/0084904 A1 | 4/2005 | Laal et al. | |
| 2012/0282181 A1 | 11/2012 | Lewinsohn et al. | |

FOREIGN PATENT DOCUMENTS

| | | | | |
|---|---|---|---|---|
| WO | WO-9904005 A1 * | 1/1999 | | G06K 14/35 |
| WO | WO-2012010875 A2 * | 1/2012 | | C07K 7/08 |
| WO | WO-2013119763 A1 * | 8/2013 | | G01N 33/54366 |

OTHER PUBLICATIONS

Khaja et al. BMC Res Notes 6:291, pp. 1-6 (Year: 2013).*

* cited by examiner

*Primary Examiner* — Oluwatosin A Ogunbiyi
(74) *Attorney, Agent, or Firm* — Hodgson Russ LLP

(57) ABSTRACT

Provided are peptides suitable for early detection of active *M. tuberculosis* (Mtb) infection in immunocompromised individuals. The peptides can form complexes with antibodies directed to Mtb antigens MS, MPT51, ESAT6 or CFPIO. Also provided are methods for detected of complexes of the peptides and the antibodies. The presence of complexes aids in predicting risk in immunocompromised individuals of developing active tuberculosis.

18 Claims, 1 Drawing Sheet
Specification includes a Sequence Listing.

SEQUENCE LISTING

```
<160> NUMBER OF SEQ ID NOS: 118

<210> SEQ ID NO 1
<211> LENGTH: 15
<212> TYPE: PRT
<213> ORGANISM: Mycobacterium tuberculosis

<400> SEQUENCE: 1

Asp Ser Phe Trp Ala Gly Val Asp Lys Val Val Ala Asp Leu Thr
1               5                   10                  15

<210> SEQ ID NO 2
<211> LENGTH: 15
<212> TYPE: PRT
<213> ORGANISM: Mycobacterium tuberculosis

<400> SEQUENCE: 2

Val Leu Asn Ala Arg Phe Ala Leu Asn Ala Ala Asn Ala Arg Trp
1               5                   10                  15

<210> SEQ ID NO 3
<211> LENGTH: 15
<212> TYPE: PRT
<213> ORGANISM: Mycobacterium tuberculosis

<400> SEQUENCE: 3

Glu Ser Pro Thr Ser Val Leu Leu Ile Asn His Gly Leu His Ile
1               5                   10                  15

<210> SEQ ID NO 4
<211> LENGTH: 15
<212> TYPE: PRT
<213> ORGANISM: Mycobacterium tuberculosis

<400> SEQUENCE: 4

His Gly Pro Ala Glu Val Ala Phe Thr Cys Glu Leu Phe Ser Arg
1               5                   10                  15

<210> SEQ ID NO 5
<211> LENGTH: 15
<212> TYPE: PRT
<213> ORGANISM: Mycobacterium tuberculosis

<400> SEQUENCE: 5

Thr Cys Glu Leu Phe Ser Arg Val Glu Asp Val Leu Gly Leu Pro
1               5                   10                  15

<210> SEQ ID NO 6
```

```
<211> LENGTH: 15
<212> TYPE: PRT
<213> ORGANISM: Mycobacterium tuberculosis

<400> SEQUENCE: 6

Ala Ala Asp Arg Val Val Phe Ile Asn Thr Gly Phe Leu Asp Arg
1               5                   10                  15

<210> SEQ ID NO 7
<211> LENGTH: 15
<212> TYPE: PRT
<213> ORGANISM: Mycobacterium tuberculosis

<400> SEQUENCE: 7

Gly Lys Arg Arg Ala Thr Ile Glu Gln Leu Leu Thr Ile Pro Leu
1               5                   10                  15

<210> SEQ ID NO 8
<211> LENGTH: 15
<212> TYPE: PRT
<213> ORGANISM: Mycobacterium tuberculosis

<400> SEQUENCE: 8

Glu Ile Arg Glu Glu Val Asp Asn Asn Cys Gln Ser Ile Leu Gly
1               5                   10                  15

<210> SEQ ID NO 9
<211> LENGTH: 15
<212> TYPE: PRT
<213> ORGANISM: Mycobacterium tuberculosis

<400> SEQUENCE: 9

Arg His Gly Val Ile Thr Ser Ala Asp Val Arg Ala Ser Leu Glu
1               5                   10                  15

<210> SEQ ID NO 10
<211> LENGTH: 15
<212> TYPE: PRT
<213> ORGANISM: Mycobacterium tuberculosis

<400> SEQUENCE: 10

Pro Met Ala Pro Asn Phe Asp Asp Ser Ile Ala Phe Leu Ala Ala
1               5                   10                  15

<210> SEQ ID NO 11
<211> LENGTH: 15
<212> TYPE: PRT
<213> ORGANISM: Mycobacterium tuberculosis

<400> SEQUENCE: 11

Ser Ile Ala Phe Leu Ala Ala Gln Glu Leu Ile Leu Ser Gly Ala
1               5                   10                  15

<210> SEQ ID NO 12
<211> LENGTH: 15
<212> TYPE: PRT
<213> ORGANISM: Mycobacterium tuberculosis

<400> SEQUENCE: 12

Val Pro Ser Pro Ser Met Gly Arg Asp Ile Pro Val Ala Phe Leu
1               5                   10                  15

<210> SEQ ID NO 13
<211> LENGTH: 15
<212> TYPE: PRT
```

<213> ORGANISM: Mycobacterium tuberculosis

<400> SEQUENCE: 13

Asp Ile Pro Val Ala Phe Leu Ala Gly Gly Pro His Ala Val Tyr
1               5                   10                  15

<210> SEQ ID NO 14
<211> LENGTH: 15
<212> TYPE: PRT
<213> ORGANISM: Mycobacterium tuberculosis

<400> SEQUENCE: 14

Gly Gly Pro His Ala Val Tyr Leu Leu Asp Ala Phe Asn Ala Gly
1               5                   10                  15

<210> SEQ ID NO 15
<211> LENGTH: 15
<212> TYPE: PRT
<213> ORGANISM: Mycobacterium tuberculosis

<400> SEQUENCE: 15

Leu Asp Ala Phe Asn Ala Gly Pro Asp Val Ser Asn Trp Val Thr
1               5                   10                  15

<210> SEQ ID NO 16
<211> LENGTH: 15
<212> TYPE: PRT
<213> ORGANISM: Mycobacterium tuberculosis

<400> SEQUENCE: 16

Asp Val Ser Asn Trp Val Thr Ala Gly Asn Ala Met Asn Thr Leu
1               5                   10                  15

<210> SEQ ID NO 17
<211> LENGTH: 15
<212> TYPE: PRT
<213> ORGANISM: Mycobacterium tuberculosis

<400> SEQUENCE: 17

Tyr Thr Asn Trp Glu Gln Asp Gly Ser Lys Gln Trp Asp Thr Phe
1               5                   10                  15

<210> SEQ ID NO 18
<211> LENGTH: 15
<212> TYPE: PRT
<213> ORGANISM: Mycobacterium tuberculosis

<400> SEQUENCE: 18

Ser Lys Gln Trp Asp Thr Phe Leu Ser Ala Glu Leu Pro Asp Trp
1               5                   10                  15

<210> SEQ ID NO 19
<211> LENGTH: 15
<212> TYPE: PRT
<213> ORGANISM: Mycobacterium tuberculosis

<400> SEQUENCE: 19

Ser Ala Glu Leu Pro Asp Trp Leu Ala Ala Asn Arg Gly Leu Ala
1               5                   10                  15

<210> SEQ ID NO 20
<211> LENGTH: 15
<212> TYPE: PRT
<213> ORGANISM: Mycobacterium tuberculosis

```
<400> SEQUENCE: 20

Pro Ala Ser Gly Asp Asn Gly Trp Gly Ser Trp Ala Pro Gln Leu
1               5                   10                  15

<210> SEQ ID NO 21
<211> LENGTH: 15
<212> TYPE: PRT
<213> ORGANISM: Mycobacterium tuberculosis

<400> SEQUENCE: 21

Asn Phe Glu Arg Ile Ser Gly Asp Leu Lys Thr Gln Ile Asp Gln
1               5                   10                  15

<210> SEQ ID NO 22
<211> LENGTH: 15
<212> TYPE: PRT
<213> ORGANISM: Mycobacterium tuberculosis

<400> SEQUENCE: 22

Glu Ser Thr Ala Gly Ser Leu Gln Gly Gln Trp Arg Gly Ala Ala
1               5                   10                  15

<210> SEQ ID NO 23
<211> LENGTH: 15
<212> TYPE: PRT
<213> ORGANISM: Mycobacterium tuberculosis

<400> SEQUENCE: 23

Gly Gln Trp Arg Gly Ala Ala Gly Thr Ala Ala Gln Ala Ala Val
1               5                   10                  15

<210> SEQ ID NO 24
<211> LENGTH: 15
<212> TYPE: PRT
<213> ORGANISM: Mycobacterium tuberculosis

<400> SEQUENCE: 24

Met Thr Glu Gln Gln Trp Asn Phe Ala Gly Ile Glu Ala Ala Ala
1               5                   10                  15

<210> SEQ ID NO 25
<211> LENGTH: 15
<212> TYPE: PRT
<213> ORGANISM: Mycobacterium tuberculosis

<400> SEQUENCE: 25

Ala Ala Trp Gly Gly Ser Gly Ser Glu Ala Tyr Gln Gly Val Gln
1               5                   10                  15

<210> SEQ ID NO 26
<211> LENGTH: 15
<212> TYPE: PRT
<213> ORGANISM: Mycobacterium tuberculosis

<400> SEQUENCE: 26

Glu Ala Tyr Gln Gly Val Gln Gln Lys Trp Asp Ala Thr Ala Thr
1               5                   10                  15

<210> SEQ ID NO 27
<211> LENGTH: 15
<212> TYPE: PRT
<213> ORGANISM: Mycobacterium tuberculosis

<400> SEQUENCE: 27
```

```
Gly Ser Phe Gly Asp Ala Thr Gly Phe Thr Val Gln Asp Gly Gln
1               5                   10                  15
```

<210> SEQ ID NO 28
<211> LENGTH: 15
<212> TYPE: PRT
<213> ORGANISM: Mycobacterium tuberculosis

<400> SEQUENCE: 28

```
Val Asp Ala Gly Leu Ala Ala Gly Phe Ser Gly Arg Ala Gln Val
1               5                   10                  15
```

<210> SEQ ID NO 29
<211> LENGTH: 15
<212> TYPE: PRT
<213> ORGANISM: Mycobacterium tuberculosis

<400> SEQUENCE: 29

```
Gly Lys Gly Ile Ser Val Val Ala Pro Ala Gly Gly Ala Tyr Ser
1               5                   10                  15
```

<210> SEQ ID NO 30
<211> LENGTH: 15
<212> TYPE: PRT
<213> ORGANISM: Mycobacterium tuberculosis

<400> SEQUENCE: 30

```
Met Thr Asp Arg Val Ser Val Gly Asn Leu Arg Ile Ala Arg Val
1               5                   10                  15
```

<210> SEQ ID NO 31
<211> LENGTH: 15
<212> TYPE: PRT
<213> ORGANISM: Mycobacterium tuberculosis

<400> SEQUENCE: 31

```
Asn Leu Arg Ile Ala Arg Val Leu Tyr Asp Phe Val Asn Asn Glu
1               5                   10                  15
```

<210> SEQ ID NO 32
<211> LENGTH: 15
<212> TYPE: PRT
<213> ORGANISM: Mycobacterium tuberculosis

<400> SEQUENCE: 32

```
Leu Pro Gly Thr Asp Ile Asp Pro Asp Ser Phe Trp Ala Gly Val
1               5                   10                  15
```

<210> SEQ ID NO 33
<211> LENGTH: 15
<212> TYPE: PRT
<213> ORGANISM: Mycobacterium tuberculosis

<400> SEQUENCE: 33

```
Lys Val Val Ala Asp Leu Thr Pro Gln Asn Gln Ala Leu Leu Asn
1               5                   10                  15
```

<210> SEQ ID NO 34
<211> LENGTH: 15
<212> TYPE: PRT
<213> ORGANISM: Mycobacterium tuberculosis

<400> SEQUENCE: 34

```
Arg Asp Glu Leu Gln Ala Gln Ile Asp Lys Trp His Arg Arg Arg
1               5                   10                  15
```

```
<210> SEQ ID NO 35
<211> LENGTH: 15
<212> TYPE: PRT
<213> ORGANISM: Mycobacterium tuberculosis

<400> SEQUENCE: 35

Ile Glu Pro Ile Asp Met Asp Ala Tyr Arg Gln Phe Leu Thr Glu
1               5                   10                  15

<210> SEQ ID NO 36
<211> LENGTH: 15
<212> TYPE: PRT
<213> ORGANISM: Mycobacterium tuberculosis

<400> SEQUENCE: 36

Tyr Arg Gln Phe Leu Thr Glu Ile Gly Tyr Leu Leu Pro Glu Pro
1               5                   10                  15

<210> SEQ ID NO 37
<211> LENGTH: 15
<212> TYPE: PRT
<213> ORGANISM: Mycobacterium tuberculosis

<400> SEQUENCE: 37

Gly Tyr Leu Leu Pro Glu Pro Asp Asp Phe Thr Ile Thr Thr Ser
1               5                   10                  15

<210> SEQ ID NO 38
<211> LENGTH: 15
<212> TYPE: PRT
<213> ORGANISM: Mycobacterium tuberculosis

<400> SEQUENCE: 38

Asp Phe Thr Ile Thr Thr Ser Gly Val Asp Ala Glu Ile Thr Thr
1               5                   10                  15

<210> SEQ ID NO 39
<211> LENGTH: 15
<212> TYPE: PRT
<213> ORGANISM: Mycobacterium tuberculosis

<400> SEQUENCE: 39

Ala Gly Pro Gln Leu Val Val Pro Val Leu Asn Ala Arg Phe Ala
1               5                   10                  15

<210> SEQ ID NO 40
<211> LENGTH: 15
<212> TYPE: PRT
<213> ORGANISM: Mycobacterium tuberculosis

<400> SEQUENCE: 40

Asn Ala Ala Asn Ala Arg Trp Gly Ser Leu Tyr Asp Ala Leu Tyr
1               5                   10                  15

<210> SEQ ID NO 41
<211> LENGTH: 15
<212> TYPE: PRT
<213> ORGANISM: Mycobacterium tuberculosis

<400> SEQUENCE: 41

Ser Leu Tyr Asp Ala Leu Tyr Gly Thr Asp Val Ile Pro Glu Thr
1               5                   10                  15
```

```
<210> SEQ ID NO 42
<211> LENGTH: 15
<212> TYPE: PRT
<213> ORGANISM: Mycobacterium tuberculosis

<400> SEQUENCE: 42

Thr Asp Val Ile Pro Glu Thr Asp Gly Ala Glu Lys Gly Pro Thr
1               5                   10                  15

<210> SEQ ID NO 43
<211> LENGTH: 15
<212> TYPE: PRT
<213> ORGANISM: Mycobacterium tuberculosis

<400> SEQUENCE: 43

Asn Lys Val Arg Gly Asp Lys Val Ile Ala Tyr Ala Arg Lys Phe
1               5                   10                  15

<210> SEQ ID NO 44
<211> LENGTH: 15
<212> TYPE: PRT
<213> ORGANISM: Mycobacterium tuberculosis

<400> SEQUENCE: 44

Ile Ala Tyr Ala Arg Lys Phe Leu Asp Asp Ser Val Pro Leu Ser
1               5                   10                  15

<210> SEQ ID NO 45
<211> LENGTH: 15
<212> TYPE: PRT
<213> ORGANISM: Mycobacterium tuberculosis

<400> SEQUENCE: 45

Asp Asp Ser Val Pro Leu Ser Ser Gly Ser Phe Gly Asp Ala Thr
1               5                   10                  15

<210> SEQ ID NO 46
<211> LENGTH: 15
<212> TYPE: PRT
<213> ORGANISM: Mycobacterium tuberculosis

<400> SEQUENCE: 46

Phe Thr Val Gln Asp Gly Gln Leu Val Val Ala Leu Pro Asp Lys
1               5                   10                  15

<210> SEQ ID NO 47
<211> LENGTH: 15
<212> TYPE: PRT
<213> ORGANISM: Mycobacterium tuberculosis

<400> SEQUENCE: 47

Val Val Ala Leu Pro Asp Lys Ser Thr Gly Leu Ala Asn Pro Gly
1               5                   10                  15

<210> SEQ ID NO 48
<211> LENGTH: 15
<212> TYPE: PRT
<213> ORGANISM: Mycobacterium tuberculosis

<400> SEQUENCE: 48

Thr Gly Leu Ala Asn Pro Gly Gln Phe Ala Gly Tyr Thr Gly Ala
1               5                   10                  15

<210> SEQ ID NO 49
<211> LENGTH: 15
```

-continued

<212> TYPE: PRT
<213> ORGANISM: Mycobacterium tuberculosis

<400> SEQUENCE: 49

Phe Ala Gly Tyr Thr Gly Ala Ala Glu Ser Pro Thr Ser Val Leu
1               5                   10                  15

<210> SEQ ID NO 50
<211> LENGTH: 15
<212> TYPE: PRT
<213> ORGANISM: Mycobacterium tuberculosis

<400> SEQUENCE: 50

Ile Asn His Gly Leu His Ile Glu Ile Leu Ile Asp Pro Glu Ser
1               5                   10                  15

<210> SEQ ID NO 51
<211> LENGTH: 15
<212> TYPE: PRT
<213> ORGANISM: Mycobacterium tuberculosis

<400> SEQUENCE: 51

Val Gly Thr Thr Asp Arg Ala Gly Val Lys Asp Val Ile Leu Glu
1               5                   10                  15

<210> SEQ ID NO 52
<211> LENGTH: 15
<212> TYPE: PRT
<213> ORGANISM: Mycobacterium tuberculosis

<400> SEQUENCE: 52

Val Lys Asp Val Ile Leu Glu Ser Ala Ile Thr Thr Ile Met Asp
1               5                   10                  15

<210> SEQ ID NO 53
<211> LENGTH: 15
<212> TYPE: PRT
<213> ORGANISM: Mycobacterium tuberculosis

<400> SEQUENCE: 53

Ala Ile Thr Thr Ile Met Asp Phe Glu Asp Ser Val Ala Ala Val
1               5                   10                  15

<210> SEQ ID NO 54
<211> LENGTH: 15
<212> TYPE: PRT
<213> ORGANISM: Mycobacterium tuberculosis

<400> SEQUENCE: 54

Glu Asp Ser Val Ala Ala Val Asp Ala Ala Asp Lys Val Leu Gly
1               5                   10                  15

<210> SEQ ID NO 55
<211> LENGTH: 15
<212> TYPE: PRT
<213> ORGANISM: Mycobacterium tuberculosis

<400> SEQUENCE: 55

Ala Ala Asp Lys Val Leu Gly Tyr Arg Asn Trp Leu Gly Leu Asn
1               5                   10                  15

<210> SEQ ID NO 56
<211> LENGTH: 15
<212> TYPE: PRT
<213> ORGANISM: Mycobacterium tuberculosis -continued

<400> SEQUENCE: 56

Arg Asn Trp Leu Gly Leu Asn Lys Gly Asp Leu Ala Ala Ala Val
1               5                   10                  15

<210> SEQ ID NO 57
<211> LENGTH: 15
<212> TYPE: PRT
<213> ORGANISM: Mycobacterium tuberculosis

<400> SEQUENCE: 57

Gly Asp Leu Ala Ala Ala Val Asp Lys Asp Gly Thr Ala Phe Leu
1               5                   10                  15

<210> SEQ ID NO 58
<211> LENGTH: 15
<212> TYPE: PRT
<213> ORGANISM: Mycobacterium tuberculosis

<400> SEQUENCE: 58

Lys Asp Gly Thr Ala Phe Leu Arg Val Leu Asn Arg Asp Arg Asn
1               5                   10                  15

<210> SEQ ID NO 59
<211> LENGTH: 15
<212> TYPE: PRT
<213> ORGANISM: Mycobacterium tuberculosis

<400> SEQUENCE: 59

Thr Ala Pro Gly Gly Gly Gln Phe Thr Leu Pro Gly Arg Ser Leu
1               5                   10                  15

<210> SEQ ID NO 60
<211> LENGTH: 15
<212> TYPE: PRT
<213> ORGANISM: Mycobacterium tuberculosis

<400> SEQUENCE: 60

Thr Leu Pro Gly Arg Ser Leu Met Phe Val Arg Asn Val Gly His
1               5                   10                  15

<210> SEQ ID NO 61
<211> LENGTH: 15
<212> TYPE: PRT
<213> ORGANISM: Mycobacterium tuberculosis

<400> SEQUENCE: 61

Phe Val Arg Asn Val Gly His Leu Met Thr Asn Asp Ala Ile Val
1               5                   10                  15

<210> SEQ ID NO 62
<211> LENGTH: 15
<212> TYPE: PRT
<213> ORGANISM: Mycobacterium tuberculosis

<400> SEQUENCE: 62

Met Thr Asn Asp Ala Ile Val Asp Thr Asp Gly Ser Glu Val Phe
1               5                   10                  15

<210> SEQ ID NO 63
<211> LENGTH: 15
<212> TYPE: PRT
<213> ORGANISM: Mycobacterium tuberculosis

<400> SEQUENCE: 63

```
Thr Asp Gly Ser Glu Val Phe Glu Gly Ile Met Asp Ala Leu Phe
1               5                   10                  15

<210> SEQ ID NO 64
<211> LENGTH: 15
<212> TYPE: PRT
<213> ORGANISM: Mycobacterium tuberculosis

<400> SEQUENCE: 64

Gly Ile Met Asp Ala Leu Phe Thr Gly Leu Ile Ala Ile His Gly
1               5                   10                  15

<210> SEQ ID NO 65
<211> LENGTH: 15
<212> TYPE: PRT
<213> ORGANISM: Mycobacterium tuberculosis

<400> SEQUENCE: 65

Gly Leu Ile Ala Ile His Gly Leu Lys Ala Ser Asp Val Asn Gly
1               5                   10                  15

<210> SEQ ID NO 66
<211> LENGTH: 15
<212> TYPE: PRT
<213> ORGANISM: Mycobacterium tuberculosis

<400> SEQUENCE: 66

Lys Ala Ser Asp Val Asn Gly Pro Leu Ile Asn Ser Arg Thr Gly
1               5                   10                  15

<210> SEQ ID NO 67
<211> LENGTH: 15
<212> TYPE: PRT
<213> ORGANISM: Mycobacterium tuberculosis

<400> SEQUENCE: 67

Ile Tyr Ile Val Lys Pro Lys Met His Gly Pro Ala Glu Val Ala
1               5                   10                  15

<210> SEQ ID NO 68
<211> LENGTH: 15
<212> TYPE: PRT
<213> ORGANISM: Mycobacterium tuberculosis

<400> SEQUENCE: 68

Glu Asp Val Leu Gly Leu Pro Gln Asn Thr Met Lys Ile Gly Ile
1               5                   10                  15

<210> SEQ ID NO 69
<211> LENGTH: 15
<212> TYPE: PRT
<213> ORGANISM: Mycobacterium tuberculosis

<400> SEQUENCE: 69

Asn Thr Met Lys Ile Gly Ile Met Asp Glu Glu Arg Arg Thr Thr
1               5                   10                  15

<210> SEQ ID NO 70
<211> LENGTH: 15
<212> TYPE: PRT
<213> ORGANISM: Mycobacterium tuberculosis

<400> SEQUENCE: 70

Asn Thr Gly Phe Leu Asp Arg Thr Gly Asp Glu Ile His Thr Ser
```

```
                1               5                   10                  15

<210> SEQ ID NO 71
<211> LENGTH: 15
<212> TYPE: PRT
<213> ORGANISM: Mycobacterium tuberculosis

<400> SEQUENCE: 71

Gly Asp Glu Ile His Thr Ser Met Glu Ala Gly Pro Met Val Arg
1               5                   10                  15

<210> SEQ ID NO 72
<211> LENGTH: 15
<212> TYPE: PRT
<213> ORGANISM: Mycobacterium tuberculosis

<400> SEQUENCE: 72

Gly Thr Met Lys Ser Gln Pro Trp Ile Leu Ala Tyr Glu Asp His
1               5                   10                  15

<210> SEQ ID NO 73
<211> LENGTH: 15
<212> TYPE: PRT
<213> ORGANISM: Mycobacterium tuberculosis

<400> SEQUENCE: 73

Ile Leu Ala Tyr Glu Asp His Asn Val Asp Ala Gly Leu Ala Ala
1               5                   10                  15

<210> SEQ ID NO 74
<211> LENGTH: 15
<212> TYPE: PRT
<213> ORGANISM: Mycobacterium tuberculosis

<400> SEQUENCE: 74

Ala Ser Thr Ala Trp Val Pro Ser Pro Thr Ala Ala Thr Leu His
1               5                   10                  15

<210> SEQ ID NO 75
<211> LENGTH: 15
<212> TYPE: PRT
<213> ORGANISM: Mycobacterium tuberculosis

<400> SEQUENCE: 75

Pro Thr Ala Ala Thr Leu His Ala Leu His Tyr His Gln Val Asp
1               5                   10                  15

<210> SEQ ID NO 76
<211> LENGTH: 15
<212> TYPE: PRT
<213> ORGANISM: Mycobacterium tuberculosis

<400> SEQUENCE: 76

Leu His Tyr His Gln Val Asp Val Ala Ala Val Gln Gln Gly Leu
1               5                   10                  15

<210> SEQ ID NO 77
<211> LENGTH: 15
<212> TYPE: PRT
<213> ORGANISM: Mycobacterium tuberculosis

<400> SEQUENCE: 77

Ala Ala Val Gln Gln Gly Leu Ala Gly Lys Arg Arg Ala Thr Ile
1               5                   10                  15
```

<210> SEQ ID NO 78
<211> LENGTH: 15
<212> TYPE: PRT
<213> ORGANISM: Mycobacterium tuberculosis

<400> SEQUENCE: 78

Gln Leu Leu Thr Ile Pro Leu Ala Lys Glu Leu Ala Trp Ala Pro
1               5                   10                  15

<210> SEQ ID NO 79
<211> LENGTH: 15
<212> TYPE: PRT
<213> ORGANISM: Mycobacterium tuberculosis

<400> SEQUENCE: 79

Lys Glu Leu Ala Trp Ala Pro Asp Glu Ile Arg Glu Glu Val Asp
1               5                   10                  15

<210> SEQ ID NO 80
<211> LENGTH: 15
<212> TYPE: PRT
<213> ORGANISM: Mycobacterium tuberculosis

<400> SEQUENCE: 80

Asn Cys Gln Ser Ile Leu Gly Tyr Val Val Arg Trp Val Asp Gln
1               5                   10                  15

<210> SEQ ID NO 81
<211> LENGTH: 15
<212> TYPE: PRT
<213> ORGANISM: Mycobacterium tuberculosis

<400> SEQUENCE: 81

Ser Gln Leu Leu Ala Asn Trp Leu Arg His Gly Val Ile Thr Ser
1               5                   10                  15

<210> SEQ ID NO 82
<211> LENGTH: 15
<212> TYPE: PRT
<213> ORGANISM: Mycobacterium tuberculosis

<400> SEQUENCE: 82

Met Ala Pro Leu Val Asp Arg Gln Asn Ala Gly Asp Val Ala Tyr
1               5                   10                  15

<210> SEQ ID NO 83
<211> LENGTH: 15
<212> TYPE: PRT
<213> ORGANISM: Mycobacterium tuberculosis

<400> SEQUENCE: 83

Glu Leu Ile Leu Ser Gly Ala Gln Gln Pro Asn Gly Tyr Thr Glu
1               5                   10                  15

<210> SEQ ID NO 84
<211> LENGTH: 15
<212> TYPE: PRT
<213> ORGANISM: Mycobacterium tuberculosis

<400> SEQUENCE: 84

Phe Lys Ala Arg Ala Ala Glu Lys Pro Ala Pro Ser Asp Arg Ala
1               5                   10                  15

<210> SEQ ID NO 85

<211> LENGTH: 15
<212> TYPE: PRT
<213> ORGANISM: Mycobacterium tuberculosis

<400> SEQUENCE: 85

Glu Lys Pro Ala Pro Ser Asp Arg Ala Gly Asp Asp Ala Ala Arg
1 5 10 15

<210> SEQ ID NO 86
<211> LENGTH: 15
<212> TYPE: PRT
<213> ORGANISM: Mycobacterium tuberculosis

<400> SEQUENCE: 86

Met Lys Gly Arg Ser Ala Leu Leu Arg Ala Leu Trp Ile Ala Ala
1 5 10 15

<210> SEQ ID NO 87
<211> LENGTH: 15
<212> TYPE: PRT
<213> ORGANISM: Mycobacterium tuberculosis

<400> SEQUENCE: 87

Ser Phe Gly Leu Gly Gly Val Ala Val Ala Ala Glu Pro Thr Ala
1 5 10 15

<210> SEQ ID NO 88
<211> LENGTH: 15
<212> TYPE: PRT
<213> ORGANISM: Mycobacterium tuberculosis

<400> SEQUENCE: 88

Ala Ala Pro Tyr Glu Asn Leu Met Val Pro Ser Pro Ser Met Gly
1 5 10 15

<210> SEQ ID NO 89
<211> LENGTH: 15
<212> TYPE: PRT
<213> ORGANISM: Mycobacterium tuberculosis

<400> SEQUENCE: 89

Gly Asn Ala Met Asn Thr Leu Ala Gly Lys Gly Ile Ser Val Val
1 5 10 15

<210> SEQ ID NO 90
<211> LENGTH: 15
<212> TYPE: PRT
<213> ORGANISM: Mycobacterium tuberculosis

<400> SEQUENCE: 90

Pro Ala Gly Gly Ala Tyr Ser Met Tyr Thr Asn Trp Glu Gln Asp
1 5 10 15

<210> SEQ ID NO 91
<211> LENGTH: 15
<212> TYPE: PRT
<213> ORGANISM: Mycobacterium tuberculosis

<400> SEQUENCE: 91

Ala Ala Asn Arg Gly Leu Ala Pro Gly Gly His Ala Ala Val Gly
1 5 10 15

<210> SEQ ID NO 92
<211> LENGTH: 15
<212> TYPE: PRT

<213> ORGANISM: Mycobacterium tuberculosis

<400> SEQUENCE: 92

Gly Gly His Ala Ala Val Gly Ala Ala Gln Gly Gly Tyr Gly Ala
1               5                   10                  15

<210> SEQ ID NO 93
<211> LENGTH: 15
<212> TYPE: PRT
<213> ORGANISM: Mycobacterium tuberculosis

<400> SEQUENCE: 93

Ala Leu Ala Ala Phe His Pro Asp Arg Phe Gly Phe Ala Gly Ser
1               5                   10                  15

<210> SEQ ID NO 94
<211> LENGTH: 15
<212> TYPE: PRT
<213> ORGANISM: Mycobacterium tuberculosis

<400> SEQUENCE: 94

Arg Phe Gly Phe Ala Gly Ser Met Ser Gly Phe Leu Tyr Pro Ser
1               5                   10                  15

<210> SEQ ID NO 95
<211> LENGTH: 15
<212> TYPE: PRT
<213> ORGANISM: Mycobacterium tuberculosis

<400> SEQUENCE: 95

Ser Gly Phe Leu Tyr Pro Ser Asn Thr Thr Thr Asn Gly Ala Ile
1               5                   10                  15

<210> SEQ ID NO 96
<211> LENGTH: 15
<212> TYPE: PRT
<213> ORGANISM: Mycobacterium tuberculosis

<400> SEQUENCE: 96

Thr Thr Thr Asn Gly Ala Ile Ala Ala Gly Met Gln Gln Phe Gly
1               5                   10                  15

<210> SEQ ID NO 97
<211> LENGTH: 15
<212> TYPE: PRT
<213> ORGANISM: Mycobacterium tuberculosis

<400> SEQUENCE: 97

Ala Gly Met Gln Gln Phe Gly Gly Val Asp Thr Asn Gly Met Trp
1               5                   10                  15

<210> SEQ ID NO 98
<211> LENGTH: 15
<212> TYPE: PRT
<213> ORGANISM: Mycobacterium tuberculosis

<400> SEQUENCE: 98

Val Asp Thr Asn Gly Met Trp Gly Ala Pro Gln Leu Gly Arg Trp
1               5                   10                  15

<210> SEQ ID NO 99
<211> LENGTH: 15
<212> TYPE: PRT
<213> ORGANISM: Mycobacterium tuberculosis

<400> SEQUENCE: 99

Ala Pro Gln Leu Gly Arg Trp Lys Trp His Asp Pro Trp Val His
1               5                   10                  15

<210> SEQ ID NO 100
<211> LENGTH: 15
<212> TYPE: PRT
<213> ORGANISM: Mycobacterium tuberculosis

<400> SEQUENCE: 100

Trp His Asp Pro Trp Val His Ala Ser Leu Leu Ala Gln Asn Asn
1               5                   10                  15

<210> SEQ ID NO 101
<211> LENGTH: 15
<212> TYPE: PRT
<213> ORGANISM: Mycobacterium tuberculosis

<400> SEQUENCE: 101

Ser Leu Leu Ala Gln Asn Asn Thr Arg Val Trp Val Trp Ser Pro
1               5                   10                  15

<210> SEQ ID NO 102
<211> LENGTH: 15
<212> TYPE: PRT
<213> ORGANISM: Mycobacterium tuberculosis

<400> SEQUENCE: 102

Asn Pro Gly Ala Ser Asp Pro Ala Ala Met Ile Gly Gln Ala Ala
1               5                   10                  15

<210> SEQ ID NO 103
<211> LENGTH: 15
<212> TYPE: PRT
<213> ORGANISM: Mycobacterium tuberculosis

<400> SEQUENCE: 103

Ala Met Gly Asn Ser Arg Met Phe Tyr Asn Gln Tyr Arg Ser Val
1               5                   10                  15

<210> SEQ ID NO 104
<211> LENGTH: 15
<212> TYPE: PRT
<213> ORGANISM: Mycobacterium tuberculosis

<400> SEQUENCE: 104

Tyr Asn Gln Tyr Arg Ser Val Gly Gly His Asn Gly His Phe Asp
1               5                   10                  15

<210> SEQ ID NO 105
<211> LENGTH: 15
<212> TYPE: PRT
<213> ORGANISM: Mycobacterium tuberculosis

<400> SEQUENCE: 105

Gly Ser Trp Ala Pro Gln Leu Gly Ala Met Ser Gly Asp Ile Val
1               5                   10                  15

<210> SEQ ID NO 106
<211> LENGTH: 15
<212> TYPE: PRT
<213> ORGANISM: Mycobacterium tuberculosis

<400> SEQUENCE: 106

Pro Gln Leu Gly Ala Met Ser Gly Asp Ile Val Gly Ala Ile Arg
1               5                   10                  15

<210> SEQ ID NO 107
<211> LENGTH: 15
<212> TYPE: PRT
<213> ORGANISM: Mycobacterium tuberculosis

<400> SEQUENCE: 107

Met Ala Glu Met Lys Thr Asp Ala Ala Thr Leu Ala Gln Glu Ala
1 5 10 15

<210> SEQ ID NO 108
<211> LENGTH: 15
<212> TYPE: PRT
<213> ORGANISM: Mycobacterium tuberculosis

<400> SEQUENCE: 108

Ala Thr Leu Ala Gln Glu Ala Gly Asn Phe Glu Arg Ile Ser Gly
1 5 10 15

<210> SEQ ID NO 109
<211> LENGTH: 15
<212> TYPE: PRT
<213> ORGANISM: Mycobacterium tuberculosis

<400> SEQUENCE: 109

Leu Lys Thr Gln Ile Asp Gln Val Glu Ser Thr Ala Gly Ser Leu
1 5 10 15

<210> SEQ ID NO 110
<211> LENGTH: 15
<212> TYPE: PRT
<213> ORGANISM: Mycobacterium tuberculosis

<400> SEQUENCE: 110

Thr Ala Ala Gln Ala Ala Val Val Arg Phe Gln Glu Ala Ala Asn
1 5 10 15

<210> SEQ ID NO 111
<211> LENGTH: 15
<212> TYPE: PRT
<213> ORGANISM: Mycobacterium tuberculosis

<400> SEQUENCE: 111

Gln Lys Gln Glu Leu Asp Glu Ile Ser Thr Asn Ile Arg Gln Ala
1 5 10 15

<210> SEQ ID NO 112
<211> LENGTH: 15
<212> TYPE: PRT
<213> ORGANISM: Mycobacterium tuberculosis

<400> SEQUENCE: 112

Ser Thr Asn Ile Arg Gln Ala Gly Val Gln Tyr Ser Arg Ala Asp
1 5 10 15

<210> SEQ ID NO 113
<211> LENGTH: 15
<212> TYPE: PRT
<213> ORGANISM: Mycobacterium tuberculosis

<400> SEQUENCE: 113

Val Gln Tyr Ser Arg Ala Asp Glu Glu Gln Gln Gln Ala Leu Ser
1 5 10 15

```
<210> SEQ ID NO 114
<211> LENGTH: 15
<212> TYPE: PRT
<213> ORGANISM: Mycobacterium tuberculosis

<400> SEQUENCE: 114

Ala Gly Ile Glu Ala Ala Ala Ser Ala Ile Gln Gly Asn Val Thr
1               5                   10                  15

<210> SEQ ID NO 115
<211> LENGTH: 15
<212> TYPE: PRT
<213> ORGANISM: Mycobacterium tuberculosis

<400> SEQUENCE: 115

Ala Ile Gln Gly Asn Val Thr Ser Ile His Ser Leu Leu Asp Glu
1               5                   10                  15

<210> SEQ ID NO 116
<211> LENGTH: 15
<212> TYPE: PRT
<213> ORGANISM: Mycobacterium tuberculosis

<400> SEQUENCE: 116

Ile His Ser Leu Leu Asp Glu Gly Lys Gln Ser Leu Thr Lys Leu
1               5                   10                  15

<210> SEQ ID NO 117
<211> LENGTH: 15
<212> TYPE: PRT
<213> ORGANISM: Mycobacterium tuberculosis

<400> SEQUENCE: 117

Lys Trp Asp Ala Thr Ala Thr Glu Leu Asn Asn Ala Leu Gln Asn
1               5                   10                  15

<210> SEQ ID NO 118
<211> LENGTH: 15
<212> TYPE: PRT
<213> ORGANISM: Mycobacterium tuberculosis

<400> SEQUENCE: 118

Leu Asn Asn Ala Leu Gln Asn Leu Ala Arg Thr Ile Ser Glu Ala
1               5                   10                  15
```

PEPTIDES OF *M. TUBERCULOSIS* FOR A SCREENING TEST FOR HIV POSITIVE PATIENTS AT HIGH-RISK FOR TUBERCULOSIS

CROSS-REFERENCE TO RELATED APPLICATIONS

This application claims priority to U.S. Provisional patent application No. 62/142,774, filed on Apr. 3, 2015, the disclosure of which is incorporated herein by reference.

STATEMENT REGARDING FEDERALLY-SPONSORED RESEARCH

This invention was made with government support under grant number R21 AI094658 awarded by the National Institutes of Health. The government has certain rights in the invention.

FIELD OF THE DISCLOSURE

This disclosure relates generally to the field of *tuberculosis*, and in particular to immunocompromised individuals who are at risk of developing *tuberculosis*.

BACKGROUND OF THE DISCLOSURE

The synergistic relationship between HIV and TB has created a public health challenge of unparalleled proportions in many TB-endemic countries. HIV-infection is the single largest risk factor for progression of *Mycobacterium tuberculosis* (Mtb) infection to clinical disease and for progression of latent TB infection (LTBI) to clinical TB. The risk of TB doubles as early as in the first year after acquiring HIV-infection, much before the reduction of CD4+ T cells occurs, and continues to rise subsequently. Co-infected patients are estimated to have a 10-15% annual risk for progressing to TB; TB is the leading cause of morbidity and mortality in this population. TB is totally treatable with the existing drugs, but the lack of appropriate diagnostic tools results in identification of less than half of the HIV+TB+ patients being diagnosed before death.

Diagnosis of TB in HIV−TB+ patients: Although TB is thought in terms of LTBI or clinical disease, these are two ends of a spectrum and between the two extreme states, TB occurs as a continuum of clinical, bacteriological and immunological manifestations. In patients with LTBI, protection against Mtb infection has been achieved by cellular immune responses that lead to containment of bacteria in granulomas where they remain quiescent for long periods. When the cellular responses are unable to restrict bacterial replication, the latent Mtb begin to replicate and the latent infection progresses towards the other end of the spectrum where frank clinical TB occurs and humoral immune responses predominate. The risk of progression of a subject with LTBI to active TB disease is only 5-10% over a lifetime.

The diagnostic test that currently serves as the gold standard for TB diagnosis is culture of bacteria. However, cultures take weeks to provide results, require sophisticated labs and infrastructure, and highly trained personnel. As a result cultures cannot be used as the diagnostic tool of choice in the TB-endemic countries. Even in low-burden and high-resource countries where cultures are used for TB diagnosis, this test fails to identify 25-30% of the pulmonary and ~50% of the extrapulmonary TB cases. Nucleic acid amplification tests (NAATs) for TB are less sensitive than cultures, and still too expensive for routine use in TB endemic settings. Microscopy with decontaminated and concentrated sputum (concentrated sputum smear, CSS) is less sensitive than NAATs, and still not implementable in high burden settings. The only diagnostic test used routinely by TB control programs in TB endemic settings is microscopic examination of smears made directly from the sputum (direct sputum smear, DSS), which identifies advanced TB patients, and is the least sensitive test for TB, and misses about half the patients. X-rays provide some value as an adjunct to TB diagnosis, more so in patients with advanced TB, but are non-specific. Thus, there is no single diagnostic test that identifies all TB patients, even in immunocompetent individuals.

Based on bacterial burden in the sputum and the extent of radiographically detectable pulmonary pathology, pulmonary TB patients can be categorized into different stages in the spectrum of TB (FIG. 1). Over 90% of the TB cases occur in low-resource developing countries where patients either lack access to any diagnostic tests and are treated empirically, or TB is diagnosed by insensitive techniques like microscopic examination of smears made directly from sputum (without decontamination and concentration; DSS), light microscopes, and occasionally chest X-rays. These diagnostic tests identify TB at a much more advanced and infectious stage. Detection of bacteria by DSS requires presence of $5\text{-}10 \times 10^3$ bacteria/ml of specimen, and identifies Stage 4 TB (multibacillary, advanced TB). Stage 4 TB patients generally show extensive radiographic abnormalities ranging from extensive infiltration to cavitary lesions. Thus, stage 4 patients can have advanced, non-cavitary TB (ANC) or advanced cavitary (AC) TB.

In contrast, diagnosis of TB in industrialized, low-burden settings is based on the use of multiple highly sensitive techniques that enables diagnosis at much early stages of progression. These include a) optimized microscopy with smears made with decontaminated and concentrated specimens and fluorescence staining (this concentrated sputum smear (CSS) microscopy is ~10-fold more sensitive than DSS); b) nucleic-acid amplification tests (NAAT) which detect ~100 bacteria/ml; and c) culture of bacteria, which is ~10 fold more sensitive than CSS (10-100 bacteria/ml). The use of these multiple tests enables diagnosis of patients at an early stage of TB, designated Stage 3. The radiographic abnormalities in these paucibacillary TB patients generally range from hilar lymphadenopathy or minimal infiltration to small cavities detected primarily by CT scans. Thus, paucibacillary TB patients may have early non-cavitary (ENC) TB or early cavitary (EC) TB.

Despite use of CSS, NAAT and cultures, bacteriological confirmation for TB is not achieved in ~20-25% of the pulmonary TB cases. Treatment at this stage of TB (stage 2) is initiated empirically on the basis of clinical and/or radiological assessment and is confirmed by response to anti-TB therapy (ATT).

Patients with no clinical symptoms, no bacteriological presence and positive responses on PPD skin test or gamma interferon release assays are classified as stage 1 TB (LTBI).

Diagnosis of TB in HIV+ patients: Clinicians in high-burden settings have to rely primarily on clinical symptoms, microscopic examination of sputum smears made directly from the specimen (DSS) and X-rays for TB diagnosis since no sensitive, specific, simple and inexpensive test are currently available. Unfortunately, HIV+TB+ patients are often asymptomatic, the sputum smear is negative in over 50% of the patients, and chest x-rays show radiological abnormalities only in about 30% of the smear-negative patients. As a result, the spectrum described above for HIV-TB+ patients is not usable for HIV+TB+ patients and TB remains undiagnosed in a high proportion of HIV+ patients. Moreover, in resource-limited settings anti-retroviral therapy (ART) is initiated when CD4+ T cells are <250/mm$^3$, or when an opportunistic infection is diagnosed. Unfortunately, about 50% of TB occurs when CD4+ T cells are >250/mm$^3$, and provision of ART to patients with unrecognized TB enhances the occurrence of IRIS. Concurrent TB enhances HIV replication; early diagnosis and treatment of TB would reduce progression of HIV-infection. About half the HIV+ patients have extrapulmonary TB, and since microbiological examination requires specimens that are obtained only by invasive techniques, diagnosis of extrapulmonary TB is even more difficult.

Intensified case finding ICF: Screening of all HIV+ patients by microbiological methods (sputum-smear or culture) without prior selection by symptoms has been demonstrated to identify substantially more HIV+TB+ patients as compared to investigating only symptomatic HIV+ patients. In recognition of the increased frequency of paucibacillary TB, as well as the atypical clinical and radiological presentation of TB in HIV+TB+ patients, the World Health Organization launched the 3Is initiative for subjects at high-risk for TB in 2008. The 3Is are intensified case finding (ICF), IPT (INH preventive therapy) and TB infection control in conjunction with scale-up of ART. ICF refers to screening for TB by bacteriological detection (microscopy-smear and/or cultures) in HIV+ patients without pre-selection on the basis of clinical symptoms for TB in order to identify patients with asymptomatic TB. However, ICF requires resources for laboratory scale-up and personnel training that are unlikely to become available even for TB suspects.

Screening test for identification of HIV+ patients at high-risk for progression to TB: Since TB can occur at any time during the course of progression of HIV-infection, patients need to be screened repeatedly for asymptomatic TB. Considering the inability of the current diagnostic tests to identify both pulmonary and extrapulmonary TB even in HIV+TB+ suspects, implementing screening for identification of high-risk for TB by ICF is impossible. While INH preventive therapy (IPT) reduces the risk for progression to TB the inability to distinguish between latent TB infection (LTBI) and asymptomatic bacteriologically-negative TB affects the ability to provide IPT.

Currently there are no tests that can identify HIV+ patients who are asymptomatic but harbor in vivo bacteria that are replicating actively but are below detection limit of cultures.

SUMMARY OF THE DISCLOSURE

The disclosure provides compositions and methods for predicting the risk of or progression of active TB in immunocompromised individuals, such as HIV positive individuals. The method comprises detecting formation of complexes between certain peptides and antibodies in biological samples from individuals, wherein the antibodies are specific for epitopes of selected Mtb antigens.

For example, the disclosure provides a method for predicting risk of an asymptomatic immunocompromised individual for developing active TB based on the detection of formation of a complex of a peptide with an antibody in a biological sample, wherein the antibody is specific for an Mtb antigen MS, MPT51, ESAT6 or CFP10. If the complexes are detected then the individual can be predicted to be at high risk of developing TB. In one embodiment, the amount (or relative amount) of complexes can be compared to a reference control and if the amount is greater than the amount in the control, then the individual can be predicted to be at a high risk of developing TB. Monitoring of progression of active TB in individuals can be carried out by periodically detecting the level of complex formation. Increased amount of complexes in samples obtained at later time points is predictive of the individual progressing toward active TB status.

The peptide may be a peptide of Table 1 (SEQ ID NOs 1-29), a 10-14 amino acid fragment of a peptide of Table 1, or a peptide which has 16-20 amino acids comprising the sequence of a peptide of Table 1, a variant, a derivative, a fusion, or a multimers of one or more of the peptides.

The disclosure also provides kits for the predicting risk of developing active TB or for monitoring the progression of active TB comprising a) an antigenic composition comprising one or more of the peptides of Table 1, a 10 to 14 amino acid fragment of the peptides of Table 1, or 16-20 amino acid peptide comprising the sequence of a peptide of Table 1; a variant, a derivative, a fusion, or a multimers of one or more of the peptides, and b) reagents, and optionally instructions, for detection of antibodies which form complexes with the antigenic composition.

DETAILED DESCRIPTION OF THE DISCLOSURE

Figure 1:
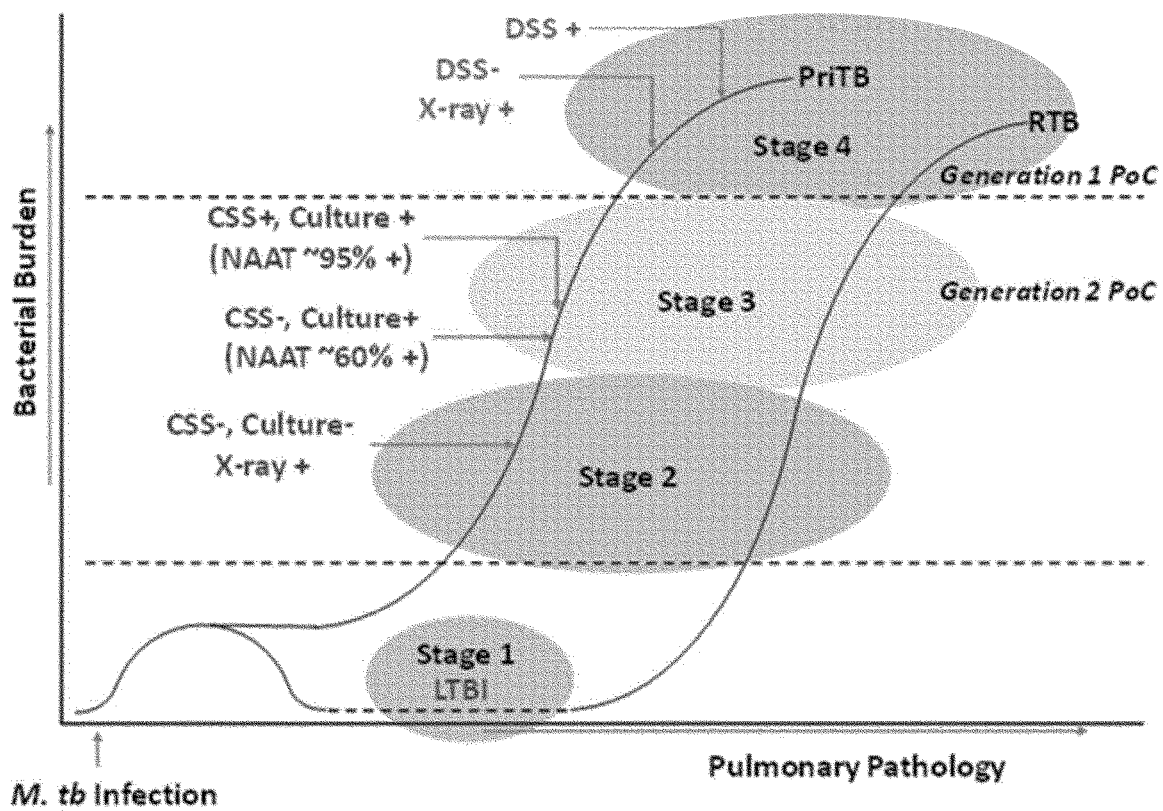
FIG. 1: Representation of bacterial burden as a function of stage of Mtb infection. The performance of current diagnostic tests at different stages of HIV positive TB positive patients is also indicated.

The present disclosure provides compositions and methods for screening for prediction of risk of developing active TB. The individual may be an immunocompromised individual. The immunocompromised individual may be an HIV positive (HIV+) individual. The individual can be an individual whose immune system is unable to control or contain the replication of Mtb. For example, immunocompromised individuals, such as, individuals infected with HIV, can be screened for the presence of antibodies to epitopes of selected Mtb antigens to identify individuals who are a high risk of developing active TB.

In one embodiment, the present disclosure provides compositions and methods for screening for the presence of actively replicating Mtb in HIV+ patients based on detection of antibodies to selected Mtb antigens. Also provided herein are compositions comprising isolated or synthesized peptides that can be used for the screening methods.

The peptides provided in the present disclosure can serve as the basis of a simple, rapid and low cost point of care (POC) screening TB test that can be used to routinely monitor asymptomatic HIV+ to identify those who are at a high risk for progressing to active TB. It is expected that early diagnosis of TB would have significant impact on TB-related morbidity and mortality in HIV+ patients, especially in TB-endemic countries. The present method can be used as a test to identify asymptomatic HIV+ patients who are at high risk for progressing to TB, in combination with ICF, and this also could impact decisions on optimal timing for provision of ART to reduce the risk of IRIS, and enable safe use of IPT to reduce the risk for progression to TB in these patients.

The present disclosure provides a method for predicting the risk of asymptomatic immunocompromised individuals progressing to active TB. For example, the method can predict the risk of asymptomatic HIV+ individuals of progressing to active TB. The method comprises contacting a biological sample obtained from an individual with a peptide and detecting the presence of a complex (also termed herein as an immune complex) formed between the peptide and an antibody present in the sample. The peptide forms a complex with an antibody that is specific for an Mtb antigen selected from the group consisting of malate synthase (MS), MPT51, ESAT6, or CFP10. The peptide can be a peptide of Table 1, a peptide which is at least a 10 amino acid long fragment of one of the peptides of Table 1, or a peptide which is from 16-20 amino acids long and contains the contiguous sequence of a peptide of Table 1. The specific peptide can also be a variant, a fusion or a multimer of these peptides as described herein. The detection of the complexes or level (amount) of complexes in the sample as compared to the amount in a reference control (relative amount) provides assessment of risk of the individual for developing active TB. The control can be a sample run in parallel or separately, without the peptide or can be a sample run in parallel or separately, with a non-specific peptide. For example, the control can be a peptide from Table 4. An increased amount of complex over the control is predictive of a risk of the individual developing active TB. In one embodiment, the method further comprises treating the individual for TB, such as, for example, by administering anti-TB medication.

The present disclosure provides a method for monitoring of HIV+ patients with latent TB infection who are asymptomatic for TB. For example, it can be used for monitoring for likelihood of reactivation of latent infection and progression to clinical TB. For this, biological samples can be obtained from the individual at different points of time, and reactivity of the samples obtained from the individual at each time point can be checked with a peptide and the presence of a complex formed between the peptide and an antibody present in the sample can be detected. The peptide is a peptide that forms a complex with an antibody that is specific for an Mtb antigen selected from the group consisting of MS, MPT51, ESAT6, or CFP10. For example, the peptide can be a peptide of Table 1, or a peptide which is at least a 10 amino acid long fragment of one of the peptides of Table 1, or a peptide which is from 16-20 amino acids long and contains the contiguous sequence of a peptide of Table 1. The specific peptide can also be a variant, a fusion or a multimer as described herein. The amount of complex formed at a later time point can be compared to an initial or earlier time point, wherein an increased amount of complex over time is an indication of likelihood that the individual is progressing toward active TB. The screening can be carried out periodically to provide a continuous monitoring of the likelihood of progression toward active TB or risk of the individual developing active TB. For example, individuals can be monitored every month, every quarter, or every year or at any frequency.

In contrast to HIV− patients, the immune dysfunction in HIV+ patients dramatically alters the clinical, bacteriological and radiological presentation of TB. The replication of bacteria is accelerated and bacterial burden increases rapidly, while pulmonary pathology is reduced and often completely absent. HIV+TB+ patients with advanced TB, who have DSS+ disease can be asymptomatic and/or have minimal radiological manifestations. A large proportion of the HIV+TB+ patients are DSS− and CSS− and can be diagnosed only by cultures. Even with cultures, a significant proportion of HIV+TB+ patients cannot be confirmed bacteriologically, especially patients who have extrapulmonary disease. And over 50% of the HIV+TB+ patients have extrapulmonary TB. The present method is useful for identifying HIV positive individuals who may have actively replication Mtb.

The present methods rely on the use of non-bacteriological markers (e.g., antibodies) rather than bacteria or bacterial components like nucleic acids/antigens etc. Detection of these markers would indicate in vivo bacterial replication in any type of the extensively heterogeneous bacterial cell types and architecture of different lesions (caseous with or without peripheral fibrosis, non-necrotizing, suppurative, fibrotic, mineralized) that are present during active TB.

The present methods and compositions are based on the delineation of antigens expressed by actively replicating Mtb in asymptomatic immunosuppressed patients. Our studies on sera from bacteriologically confirmed HIV+TB+ patients have identified 2 Mtb antigens that are highly immunodominant. We further demonstrate that antibodies to these antigens are present in ~80-90% of the HIV+TB+ patients. These antigens are Malate Synthase (MS) (encoded by Mtb gene Rv1837c), and MPT51 (encoded by Mtb gene Rv3803c). We observed that anti-MS and anti-MPT51 antibodies are present at all levels of CD4+ T cells in HIV+ patients, and are present in HIV+ pulmonary and extrapulmonary TB patients.

Studies with stored retrospective sera obtained from asymptomatic HIV+ patients who subsequently progressed to TB also showed that these sera have antibodies to MS and MPT51. In addition, two other Mtb proteins to which antibodies are detectable ~6-12 months prior to clinical progression of asymptomatic HIV+ patients to TB were identified as ESAT6 (encoded by Mtb gene Rv3875) and CFP10 (encoded by Mtb gene Rv3874).

Based on the data and description provided herein, the present disclosure provides compositions and methods directed to detection of antibodies that recognize one or more epitopes of MS and/or MPT51 and/or ESAT6 and/or CFP10.

The amino acid sequence of MS full length protein is available at GenBank Accession number P9WK17, the amino acid sequence MPT51 full length protein is available at GenBank Accession number CAA05211, the amino acid sequence of ESAT6 full length protein is available at GenBank Accession number ABD98028, and the amino acid sequence of CFP10 full length protein is available at GenBank Accession number CCP46703.

In one embodiment, this disclosure provides a method for detecting and/or quantitating antibodies reactive against epitopes of MS, MPT51, ESAT6 and/or CFP10 to identify HIV positive individuals harboring actively replicating Mtb. In one embodiment, the detection is carried out prior to onset of symptomatic TB or before TB is bacteriologically confirmed. The antibodies are detected by using certain fragments of the full length proteins, variants of the fragments, derivatives of the fragments or variants, or multimers of the fragments, variants, or derivatives. The method provides a method of detecting and/or quantitating immune complexes of the peptides and antibodies reactive against epitopes of MS, MPT51, ESAT6 and/or CFP10.

Accordingly, in one aspect, this disclosure provides peptides which are fragments of MS, MPT51, ESAT6 and CFP10, and which are recognized by antibodies found in HIV positive patients who are harboring actively replicating Mtb but have not developed any symptoms for TB. In one embodiment, these antibodies are not detected in LTBI patients.

In one embodiment, the present disclosure provides peptides which are up to 15 amino acids long and have the sequences shown in Table 1 below.

TABLE 1

| Name | ID | SEQ ID NO: |
|---|---|---|
| Rv1837c_0033 | DSFWAGVDKVVADLT | 1 |
| Rv1837c_0121 | VLNARFALNAANARW | 2 |
| Rv1837c_0225 | ESPTSVLLINHGLHI | 3 |
| Rv1837c_0401 | HGPAEVAFTCELFSR | 4 |
| Rv1837c_0409 | TCELFSRVEDVLGLP | 5 |
| Rv1837c_0449 | AADRVVFINTGFLDR | 6 |
| Rv1837c_0569 | GKRRATIEQLLTIPL | 7 |
| Rv1837c_0593 | EIREEVDNNCQSILG | 8 |
| Rv1837c_0649 | RHGVITSADVRASLE | 9 |
| Rv1837c_0681 | PMAPNFDDSIAFLAA | 10 |
| Rv1837c_0689 | SIAFLAAQELILSGA | 11 |
| Rv3803c_0041 | VPSPSMGRDIPVAFL | 12 |
| Rv3803c_0049 | DIPVAFLAGGPHAVY | 13 |
| Rv3803c_0057 | GGPHAVYLLDAFNAG | 14 |
| Rv3803c_0065 | LDAFNAGPDVSNWVT | 15 |
| Rv3803c_0073 | DVSNWVTAGNAMNTL | 16 |
| Rv3803c_0105 | YTNWEQDGSKQWDTF | 17 |
| Rv3803c_0113 | SKQWDTFLSAELPDW | 18 |
| Rv3803c_0121 | SAELPDWLAANRGLA | 19 |
| Rv3803c_0273 | PASGDNGWGSWAPQL | 20 |
| Rv3874-0017 | NFERISGDLKTQIDQ | 21 |
| Rv3874-0033 | ESTAGSLQGQWRGAA | 22 |
| Rv3874_0041 | GQWRGAAGTAAQAAV | 23 |
| Rv3875_0001 | MTEQQWNFAGIEAAA | 24 |
| Rv3875_0041 | AAWGGSGSEAYQGVQ | 25 |
| Rv3875_0049 | EAYQGVQQKWDATAT | 26 |
| Rv1837c_0185 | GSFGDATGFTVQDGQ | 27 |
| Rv1837c_0497 | VDAGLAAGFSGRAQV | 28 |
| Rv3803c_0089 | GKGISVVAPAGGAYS | 29 |

The Rv1837c peptides (SEQ ID NOs 1-11, 27, 28) are fragments of MS, the Rv3803c peptides (SEQ ID NOs 12-20) are fragments of MPT51, the Rv3874 peptides (SEQ ID NOs 21-23, 29) are fragments of ESAT6, and the Rv3875 peptides (SEQ ID NOs 24-26) are fragments of CFP10. The peptides are not the full length proteins from which they are derived. In one embodiment, the peptides are purified peptides.

In one embodiment, the disclosure provides peptides which are fragments of the peptides disclosed in Table 1. For example, the fragments may be peptides which are at least 10 amino acid long. In specific embodiments, the peptide fragments consist of 10, 11, 12, 13, and 14 amino acids out of the 15 amino acid peptides of Table 1.

In one embodiment, the peptides of the present invention are from 16-20 amino acid long and comprise the contiguous sequence of a peptide of Table 1.

In one embodiment, the peptides may be variants of the peptides disclosed herein, which bind to antibodies to MS, MPT51, ESAT6 or CFP10. In one embodiment, the variants contain conservative amino acid substituents. In various embodiments one, two, three, four, or five different amino acids are substituted. The term "conservative substitution" is used to reflect amino acid substitutions that do not substantially alter the Mtb antibody binding activity of the peptide. Typically conservative amino acid substitutions involve substitution of one amino acid for another amino acid with similar chemical properties (e.g. charge or hydrophobicity). Conservative substitutions include, but are not limited to Gly/Ala; Arg/Lys; Ser/Tyr/Thr; Leu/Ile/Val; Asp/Glu; Gln/Asn; and Phe/Trp/Tyr. Other examples of substitutions are: Gly/Ala/Pro; Tyr/His; Arg/Lys/His; Ser/Thr/Cys; and Leu/Ile/Val/Met. Substitution can also be in the form of analog substitutions where a standard amino acid is replaced by a non-standard amino acid such as a synthetic or rare amino acid differing minimally from the parent residue from which it is typically derived.

In one embodiment, the disclosure provides fusion polypeptide which may be a fusion of two or more of the peptides disclosed in Table 1, and which fusion polypeptide binds to an antibody that is specific for MS, MPT51, ESAT6 or CFP10.

In one embodiment, the disclosure provides multimers which may comprise two or more units of the same peptide from Table 1, or variants thereof, and which multimers bind to an antibody that is specific for MS, MPT51, ESAT6 or CFP10.

The fusion polypeptide may combine one or more peptide units derived from one or more of Mtb proteins selected from the group consisting of MS, MPT51, ESAT6 and CFP10. In one embodiment, the fusion polypeptide comprises a variant of the peptides. The fusion polypeptide may include one or more linkers linking any two or more of the individual peptides or variants thereof. Any peptide linker known in the art maybe used, including those cleavable by any of a number of proteolytic enzymes.

In one embodiment, the peptide multimer has the formula:

$$P^1_n$$

wherein P1 is any of the above peptides or the fragment or substitution variant thereof, and n=2-8.

In one embodiment, a peptide multimer has the formula:

$$(P^1-X_m)_n-P^2$$

wherein P1 and P2 are any of the above peptides or fragments thereof or substitution variants thereof, and wherein:

(i) P¹ and P² may be the same or different and each occurrence of P¹ in the P¹—X$_m$ structure may be a different peptide, fragment or variant from its adjacent neighbor; and (ii) X is (A) C1-C5 alkyl, C1-C5 alkenyl, C1-C5 alkynyl, C1-C5 polyether containing up to 4 oxygen atoms, wherein m=0 or 1, and, n=1-7; or (B) Glyz wherein m=0 or 1, and, z=1-6, and wherein the peptide multimer reacts with an antibody specific for the Mtb protein of which any included peptide is a fragment.

In one embodiment, the antigenic composition is a recombinant peptide multimer having the formula:

$$(P^1\text{-}Gly_z)_n—P^2$$

wherein $P^1$ and $P^2$ are any of the above peptides or the fragment or substitution variant thereof, and wherein (a) $P^1$ and $P^2$ may be the same or different and each occurrence of P1 in the P1-Glyn structure may be a different peptide or variant from its adjacent neighbor;

(b) n=1-100 and z=0-6, and wherein the peptide multimer reacts with an antibody specific for the Mtb protein of which any included peptide is a fragment.

In one embodiment the present disclosure provides peptides, fragments thereof, fusion polypeptides thereof or multimers thereof, as disclosed herein, which are modified by covalent attachment to carriers such as keyhole limpet hemocyanin (KLH), bovine serum albumin (BSA), rabbit serum albumin (RSA) and the like. Conjugation to these carriers can be achieved via an N-terminal cysteine or C-terminal cysteine amide residue added to the peptide's sequence. Thus, in one embodiment, the present disclosure provides peptides, fragments thereof, fusion polypeptides thereof or multimers thereof which has a N-terminal and/or a C-terminal cysteine. Other carriers such as ovalbumin, thyroglobulin, tetanus toxoid, diphtheria toxoid, tuberculin PPD may also be used. In one embodiment, the carrier is a nanoparticle, such as, for example, a gold nanoparticle. In one embodiment, the peptides, fragments thereof, fusion polypeptides thereof or multimers thereof are purified. In one embodiment, the only peptides or proteins attached to the carriers are the peptides disclosed herein.

The peptides, fragments, variants, derivatives or multimers disclosed herein can be present in solution. In one embodiment, the peptides, fragments, variants, derivatives, or multimers disclosed herein are present as attached to a solid substrate. In one embodiment, the only peptides attached to the solid substrate are peptides of Table 1.

In one embodiment, the present disclosure provides peptides of Table 1, peptides that are 10-14 amino acid fragments of the peptides of Table 1, or which are 16-20 amino acids long and comprise the sequence of a peptide of Table 1, variants thereof, derivatives thereof, multimers thereof, or fusion polypeptides thereof immobilized on a solid phase support. The solid phase support may be any support capable of binding antigens or antibodies, and includes microparticles, nanoparticles, beads, porous and impermeable strips and membranes, the interior surface of a reaction vessel such as an eppendorf tube, test tube or any type of ELISA plate, the external surface of a rod, microarray slides and the like. The solid phase support may be made of glass, polystyrene, polypropylene, polyethylene, dextran, nylon, amylases, natural and modified celluloses, polyacrylamides, polyvinylidene difluoride, agaroses such as Sepharose®, and magnetic beads and the like.

The peptides of the invention may be prepared using recombinant DNA technology. Alternatively, the shorter peptides may be prepared using solid-phase synthesis, such as that generally described by Merrifield, J. Amer. Chem. Soc., 85:2149-54 (1963), although other equivalent chemical syntheses known in the art may also be used. Solid-phase peptide synthesis may be initiated from the C-terminus (or N-terminus) of the peptide by coupling a protected α-amino acid to a suitable resin. Such a starting material can be prepared by attaching an α-amino-protected amino acid by an ester linkage to a chloromethylated resin or to a hydroxymethyl resin, or by an amide bond to a BHA (benzhydrylamine hydrochloride salt) resin or MBHA (4-methylbenzhydrylamine hydrochloride salt) resin. Such methods, well-known in the art, are disclosed, for example, in U.S. Pat. No. 5,994,309.

In one embodiment, the C-terminus or N-terminus of the peptide can be modified to provide C-terminus functionalized or N-terminus functionalized peptides. The C-terminus carboxyl group (—C(O)OH) can be reacted to form functional groups such as, for example, acyl halides, anhydrides, esters, lactones, amides, lactams, nitriles, ketones, and alcohols. The N-terminus amine group (a amine, —$NH_2$) can be reacted to form functional groups such as, for example, amides, carbamates, substituted ureas, substituted amines, imines (e.g., a substituted imine), and N-oxide groups. The C-terminus functionalized or N-terminus functionalized peptides can be reacted to form other functional groups or used to form peptide conjugates with other molecules.

In one embodiment, one or more of the peptides, fragments, variants, fusions, derivatives, multimers as disclosed herein are provided in compositions suitable for use in affinity/binding assays. For example, the peptides may be provided in suitable buffers, including, but not limited to, phosphate buffers, TRIS buffers and the like.

In one embodiment, the present disclosure provides solid phase substrates, to which have been immobilized peptides, fragments thereof, variants thereof, fusions thereof, derivatives thereof, or multimers of peptides from MS, MPT51, ESAT6 and/or CFP10. In one embodiment, the disclosure provides a solid substrate on which are immobilized peptides or fragments thereof, of Table 1. In one embodiment, the substrate is a multiwell plate. The peptides may by immobilized by covalent linkage or by adsorbing on to any substrate line poly-lysine etc.

In one embodiment, this disclosure provides a complex of an antibody to MS, MPT51, ESAT6 and/or CFP10, with a peptide derived from its respective antigenic protein. The complexes may be present in a buffer (such as a physiological buffer), which may comprise a biological sample. The fluid sample containing the complexes may or may not contain free antibodies that are not part of the complexes. For example, in one embodiment, this disclosure provides a complex of an antibody to MS with a peptide that is 10-20 amino acids and contains a contiguous sequence disclosed in one or more peptides of the MS peptides as provided in Table 1 (SEQ ID NOs 1-11, 27, 28). In one embodiment, the complex is formed of a MS peptide from Table 1 (SEQ ID NOs 1-11, 27, 28) with an antibody to MS.

In one embodiment, this disclosure provides a complex of an antibody to MPT51 with a peptide that is 10-20 amino acids and contains a contiguous sequence disclosed in one or more peptides of MPT51 as provided in Table 1 (SEQ ID NOs 12-20). In one embodiment, the complex is formed of a MPT51 peptide from Table 1 (SEQ ID NO: 12-20) with an antibody to MPT51.

In one embodiment, this disclosure provides a complex of an antibody to ESAT6 with a peptide that is 10-20 amino acids and contains a contiguous sequence disclosed in one or more peptides of ESAT6 as provided in Table 1 (SEQ ID NOs 21-23, 29). In one embodiment, the complex is formed of a ESAT6 peptide from Table 1 (SEQ ID NO. 21-23, 29) with an antibody to ESAT6.

In one embodiment, this disclosure provides a complex of an antibody to CFP10 with a peptide that is 10-20 amino acids and contains a contiguous sequence disclosed in one or more peptides of CFP10 as provided in Table 1 (SEQ ID NOs 24-26). In one embodiment, the complex is formed of a CFP10 peptide from Table 1 (SEQ ID NO. 24-26) with an antibody to CFP10.

In one embodiment, the present disclosure provides a composition comprising a complex of a peptide and an antibody specific for MS, MPT51, ESAT6 or CFP10 in a buffer, such as a phosphate buffer, TRIS buffer or any other buffer routinely used in binding assays or for storage.

The present peptides and compositions can be used to detect the presence of antibodies in biological samples obtained from individuals. The solid phase substrates having peptides, fragments, variants or multimers immobilized thereon, can be used for capture of antibodies in urine, serum, plasma or other body fluid specimens from individuals. The complexes of MS, MPT51, ESAT6, or CFP10 antibodies and a peptide, fragment, variant, derivative or multimer as disclosed herein, can be used in the detection of antibodies to epitopes of MS, MPT51, ESAT6, or CFP10 in specimens. For example, these complexes can be used to detect or quantitate the amount of such antibodies in patient samples.

In one embodiment, the present disclosure provides a method for detecting the presence of an antibody to epitopes of MS, MPT51, ESAT6, or CFP10 proteins in a specimen from an individual. In the method, a composition comprising one or more peptides or variants thereof, derivatives thereof or multimers thereof (generally referred to herein as antigen) is brought in contact with a solid support or carrier, as disclosed herein, allowing the antigen to adsorb and become immobilized to the solid support. The immobilized antigen is then allowed to interact with the biological fluid sample suspected of containing anti-Mtb antibodies, under conditions such that any specific antibodies in the sample bind to the immobilized antigen. Unbound materials are removed (such as by washing with suitable buffers) and the bound antibodies are detected by using a detectably labeled binding partner that specifically binds to the antibodies bound to the antigen or to the antigen-antibody complex. The binding partner thus binds to the immobilized antibody allowing their detection. Detection of the label is a measure of the immobilized antibody. For example, a second antibody, such as a fluorescently labeled or enzymatically labeled (alkaline phosphatase, horse-radish peroxidase, B galactosidase etc) anti-immunoglobulin antibody produced in a different species (such as a detectably labeled goat anti-human immunoglobulin) may be used. In one embodiment, the solid support is a microarray slide or a multiwell cluster.

The detectable label may be any one routinely used in the art. In one embodiment, the detectable label may be a fluorophore, such as fluorescein isothiocyanate, rhodamine, phycoerythrin, phycocyanin, allophycocyanin, o-phthaldehyde, fluorescamine or fluorescence-emitting metals such as $^{152}$Eu or other lanthanides. These metals are attached to antibodies using metal chelators. In one embodiment, the detectable label is a chemiluminescent compound. The presence of a chemiluminescent-tagged antibody or antigen is then determined by detecting the luminescence that arises during the course of a chemical reaction. Examples of useful chemiluminescent labeling compounds are luminol, isoluminol, theromatic acridinium ester, imidazole, acridinium salt and oxalate ester. Examples of bioluminescent compounds include luciferin, luciferase and aequorin. In one embodiment, the detectable label may be a radiolabel such as $^{125}$I, $^{131}$I, $^{35}$S, $^{3}$H and $^{14}$C.

The second antibody may be specific for epitopes characteristic of a particular human immunoglobulin isotype, for example IgM, IgG$_1$, IgG$_{2a}$, IgA and the like, thus permitting identification of the isotype or isotypes of antibodies in the sample which are specific for the mycobacterial antigen. Alternatively, the second antibody may be specific for an idiotype of the anti-Mtb antibody of the sample.

Other binding partners for detection of the sample antibody include staphylococcal immunoglobulin binding proteins (such as, for example, protein A), staphylococcal protein G, or a combination thereof. Protein G binds to the Fc portion of Ig molecules as well as to IgG Fab fragment at the V$_H$3 domain. Protein C of *Peptococcus magnus* binds to the Fab region of the immunoglobulin molecule. Other examples are microbial immunoglobulin binding proteins, for example from Streptococci.

Using any of the assays described herein, those skilled in the art will be able to determine operative and optimal assay conditions for each determination by employing routine experimentation. Furthermore, other steps as washing, stirring, shaking, filtering and the like may be added to the assays as is customary or necessary for the particular situation.

In one embodiment, enzyme-linked immunosorbent assay (ELISA) can be used, where an enzyme is used as a detectable label bound to either an antibody or antigen. When exposed to its substrate, the enzyme reacts to produce a chemical moiety which can be detected, for example, by spectrophotometric, fluorometric or visual means. Examples of enzymes which can be used to detectably label the reagents useful in the present invention include, but are not limited to, horseradish peroxidase, alkaline phosphatase, glucose oxidase, β-galactosidase, ribonuclease, urease, catalase, malate dehydrogenase, staphylococcal nuclease, asparaginase, Δ-5-steroid isomerase, yeast alcohol dehydrogenase, α-glycerophosphate dehydrogenase, triose phosphate isomerase, glucose-6-phosphate dehydrogenase, glucoamylase and acetylcholinesterase.

In one embodiment, the peptides are not immobilized on a solid support, but can be used in a solution based assay for detection of antibodies. Such assays are well known in the art and comprise contacting the antigen with a test sample to allow formation of antigen-antibody complexes. A detectably labeled binding partner (such as a second antibody directed toward the first antibody from the sample) may be used to precipitate the complex. Detection of the label provides a measure of the presence of antibodies in the sample.

In one embodiment, the present disclosure provides a method for detecting the presence a complex of a peptide from Table 1, fragment or variant thereof, or a multimer or fusion peptide and an antibody that is specific for MS, MPT51, ESAT6, CFP10, or an epitope thereof in a fluid sample. The fluid sample may be a biological sample or may contain a biological sample (such as a sample—diluted or undiluted—from an individual). In the method, the complex, which may be immobilized to a solid support or carrier, is detected by contacting with a detectably labeled binding partner that specifically binds to the antibodies of the complex or that specifically binds to the peptide, fragment, variant, multimer or fusion peptide, at a different location than the antibodies from the sample. The binding partner thus binds to the complex allowing their detection. The complex with the detectable binding partner may be precipitated. Detection of the label is a measure of the peptide-antibody complex. For example, a second antibody, such as a fluorescently labeled or enzymatically labeled (alkaline phosphatase, horse-radish peroxidase, B galactosidase etc) anti-immunoglobulin antibody produced in a different species (such as a detectably labeled goat anti-human immunoglobulin) may be used. In one embodiment, the solid support is a microarray slide or a multiwell cluster.

While the present method can be used as point of care type of method on fresh specimens, the specimens may also be refrigerated or frozen and later retrieved for testing. The specimen may be any biological sample comprising a biological fluid from an individual. The biological fluid sample may comprise cellular materials or may be free of cellular materials. Examples of biological fluids include, blood, serum, plasma, pleural fluid, vitreous fluid, sputum, saliva, urine and the like. The biological samples may be used undiluted or they may be diluted as desired. In one embodiment, the samples are concentrated. Cellular components, if present in the samples, may be removed prior to assaying.

In one embodiment, the only peptides contained in the compositions and methods described herein are the peptides of Table 1, fragments, multimers, fusion peptides, or variants disclosed herein.

In one embodiment, the disclosure provides a method for early detection of active Mtb infection in an individual, who may be an immunocompromised individual, such as an HIV positive individual, comprising contacting a biological sample obtained from the individual with a peptide of Table 1 (SEQ ID NOs 1-34), a 10-14 amino acid fragment thereof, a peptide that comprises the sequence of a peptide of table 1, a variant, a fusion, a derivative, or a mutimer thereof, and detecting the presence of a complex formed of the Mtb peptide with antibodies present in the sample. The antibodies may be directed towards epitopes of MS, MPT51, ESAT6 and/or CFP10. The peptide may be in solution or may be immobilized on a solid support. The asymptomatic individual may not show the presence of TB as assayed by one or more of DSS, CSS, NAAT or bacterial culture. The biological sample in which the presence of antibodies is being detected can be any biological sample, including, but not limited to blood, serum, plasma, urine, pleural fluid, ocular fluid or saliva. The complex of the peptide and the antibody (also termed herein as an immune complex) may be detected by using a detectably labeled second antibody that specifically binds to the anti-Mtb peptide antibody. The method is suitable for detecting pulmonary as well as extrapulmonary Mtb infection. The individual generally has an active Mtb infection and may have an immune system that is unable to control or contain the replication of Mtb.

In one embodiment, the disclosure provides a solid support having immobilized thereon one or more peptides described in Table 1, one or more peptides that are 10-14 amino acid fragments of the peptides of table 1, 16-20 amino acid peptides that comprise the sequence of a peptide of Table 1, or a variant, derivative, fusion, or mutilmer of the peptides, or combinations of the foregoing. The peptide or peptides may be immobilized by covalent or non-covalent linkage. The solid support can be a microarray slide. In one embodiment, the only peptides immobilized on the solid support are peptides described in Table 1, one or more peptides that are 10-14 amino acid fragments of the peptides of table 1, or 16-20 amino acid peptides that comprise the sequence of a peptide of Table 1

The disclosure also provides a complex of a peptide selected from the group disclosed in Table 1, a peptide that is a 10-14 amino acid fragment of the peptides of table 1, a 16-20 amino acid peptide that comprises the sequence of a peptide of Table 1, with an antibody that is specific for an epitope of MS MPT51, ESAT6, CFP10. The Mtb protein can be MS and the peptide can be selected from the group consisting of SEQ ID NOs 1-11, 27 and 28. The Mtb protein can be MPT51 and the peptide can be selected from the group consisting of SEQ ID NOs 12-20. The Mtb protein can be ESAT6 and the peptide can be selected from the group consisting of SEQ ID NOs 21-23 and 29. The Mtb protein is CFP10 and the peptide can be selected from the group consisting of SEQ ID NOs 24-26. The complex of the peptide and antibody can be present in a buffer.

The disclosure also provides kits for use in predicting risk of developing active TB or for monitoring the progression of active TB comprising: an antigenic composition comprising one or more of the peptides of Table 1, a 10 to 14 amino acid fragment of the peptides of Table 1, or 16-20 amino acid peptide comprising the sequence of a peptide of Table 1, variants thereof, fusions, thereof, derivatives thereof, or multimers thereof; and b) reagents for detection of antibodies which form complexes with the antigenic composition of a).

The following statements are provided as illustrations of the disclosure:

Statement 1: A method for early detection of active Mtb infection in an individual comprising: contacting a biological sample obtained from the individual with a peptide of Table 1 (SEQ ID NOs 1-29), a 10-14 amino acid fragment of a peptide of Table 1, a peptide which has 16-20 amino acids comprising the sequence of a peptide of Table 1, a variant, a derivative, multimers or a fusion of any of the preceding peptides; and detecting the formation of a complex of the peptide with antibodies present in the sample, wherein formation of the complex is an indication of active Mtb infection in the individual.

Statement 2: The method of claim 1, wherein the individual is an immunocompromised individual, such as an HIV positive individual.

Statement 3: The method of any of the preceding claims wherein the peptide of Table 1 is immobilized on a solid support.

Statement 4: The method of any of the preceding claims, wherein the individual does not show the presence of TB as assayed by DSS, CSS, NAAT or bacterial culture.

Statement 5: The method of any of the preceding claims, wherein the biological sample is blood, serum, plasma, urine, pleural fluid, ocular fluid or saliva.

Statement 6: A method for predicting risk of an asymptomatic immunocompromised individual developing active tuberculosis (TB) comprising: a) contacting a biological sample obtained from the individual with a peptide selected from the group consisting of: a peptide of Table 1 (SEQ ID NOs 1-29), a 10-14 amino acid fragment of a peptide of Table 1, a peptide which has 16-20 amino acids comprising the sequence of a peptide of Table 1, variants thereof, fusions thereof, or derivatives or multimers thereof; b) detecting the presence of a complex formed of the peptide with the an antibody in the sample, wherein the antibody is specific for an Mtb antigen selected from the group consisting of MS MPT51, ESAT6 and CFP10; c) comparing the level of complexes in the sample to the level of complexes in a control; d) identifying the individual to be at risk of developing active TB if the level of complexes in the sample from the individual is more than the level of complexes in the control.

Statement 7: The method of Statement 6, wherein the individual is HIV positive.

Statement 8: The method of Statements 6 or 7, wherein the control is a peptide of Table 4.

Statement 9: The method of any one of Statements 6 to 8, wherein the presence of the complex is detected by using a detectably labeled second antibody that is specific for the antibody in the sample.

Statement 10: The method any one of Statements 6 to 9, wherein the individual does not show the presence of TB as assayed by direct sputum smear, concentrated sputum smear, nucleic acid amplification test, or bacterial culture.

Statement 11: The method of one of Statements 6 to 10, wherein the biological sample is blood, serum, plasma, urine, pleural fluid, ocular fluid or saliva.

Statement 12: A method of monitoring the progression of tuberculosis (TB) in an immunocompromised individual comprising: a) contacting each of at least two biological samples obtained from the individual at two different times with a peptide selected from the group consisting of a peptide of Table 1 (SEQ ID NOs 1-29), a 10-14 amino acid fragment of a peptide of Table 1, a peptide which has 16-20 amino acids comprising the sequence of a peptide of Table 1, variants thereof, fusions thereof, or derivatives or multimers thereof; b) detecting the formation of a complex of the peptide with an antibody present in the sample, wherein the antibody is specific MS MPT51, ESAT6, CFP10; c) comparing the level of the complexes in the two samples; and d) if the level of the complexes is more in the sample obtained at the later time, identifying the individual as progressing toward active TB.

Statement 13: The method of Statement 12, wherein the individual is HIV+.

Statement 14: The method of Statements 12 or 13, wherein the presence of the complex is detected by using a detectably labeled second antibody that is specific for the antibody in the sample.

Statement 15: The method of any one of Statements 12 to 14, wherein the biological sample is blood, serum, plasma, urine, pleural fluid, ocular fluid or saliva.

Statement 16: A solid support having immobilized thereon one or more peptides of Table 1, one or more peptides which are 10-14 amino acid fragments of the peptides of Table 1, peptides which are 16-20 amino acids and contain the sequence of a peptide of Table 1, combinations thereof, variants thereof, fusions thereof, or derivatives or multimers thereof.

Statement 17: The solid support of Statement 16, wherein the peptides are immobilized by covalent or non-covalent linkage.

Statement 18: A kit for identifying risk of developing active tuberculosis (TB) or for monitoring the progression of active TB comprising: a) an antigenic composition comprising one or more of the peptides of Table 1, a 10 to 14 amino acid fragment of the peptides of Table 1, or 16-20 amino acid peptide comprising the sequence of a peptide of Table 1, variants thereof, fusions thereof, or derivatives or multimers thereof; and b) reagents for detection of antibodies which form complexes with the antigenic composition of a).

Statement 19: The method of any one of Statements 1 to 15, further comprising administering medication to the individual for the treatment of TB and/or HIV, or slowing the progress of TB.

The invention is further described through the following example, which is intended to be illustrative and not restrictive.

Example 1

This example provides the results of prospective studies with sera from asymptomatic HIV+ patients who progressed to clinical TB and were put on ATT. We conducted these prospective studies in HIV+ patients in India, which contributes a third of the global burden of TB and where 60~80% of the urban population is estimated to have LTBI, making this an ideal geographical location for the prospective studies.

The patients were recruited from an immunodeficiency clinic. Patients were screened for HIV infection by ELISA; those testing HIV+ were confirmed by 2 rapid tests provided by National AIDS Control Organization (NACO). Confirmed HIV+ patients were subjected to routine hematological investigations, (CBC, ESR, CD4+ T cell counts), liver function tests (SGOT/SGPT, Alkaline phosphatase), renal function tests (blood urea, serum creatinine), blood sugar, chest X ray, VDRL, HBs Ag, Anti HCV Abs).

Figure 2:
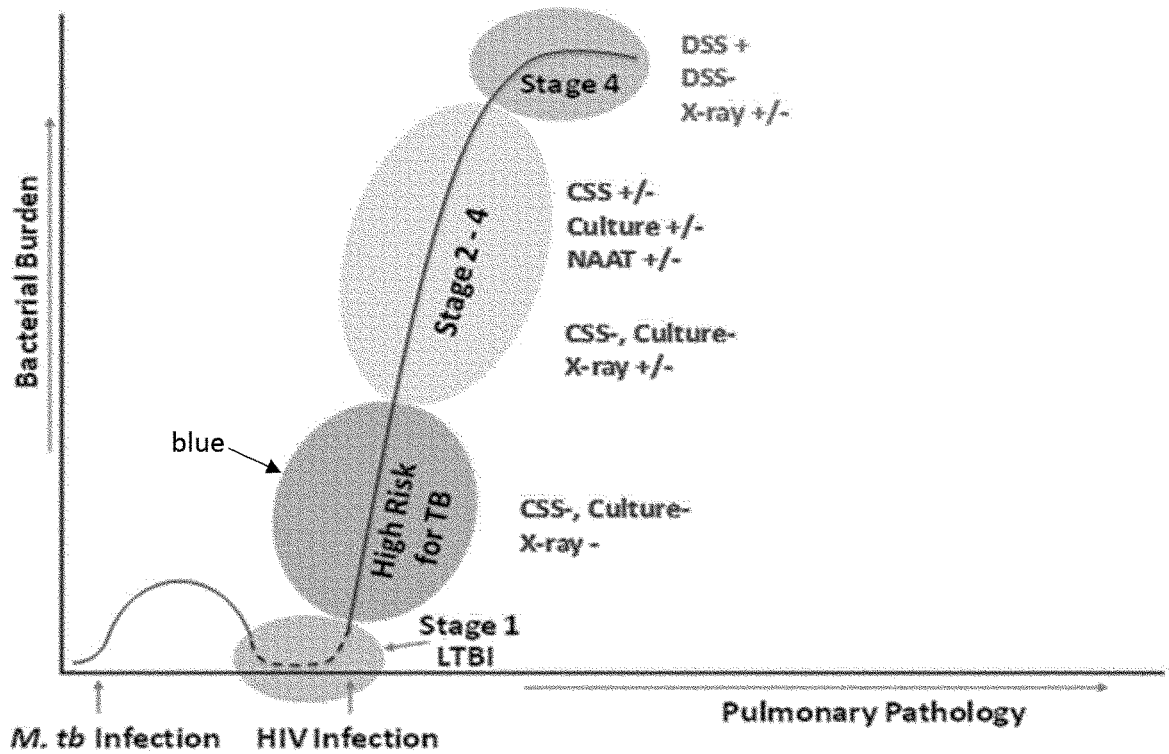
FIG. 2: Representation of the dysfunctional immune system of HIV+ patient. The immune system is unable to control Mtb latent infection, resulting in ~500 fold higher risk of progression of latent TB to active TB. The course of TB is accelerated and yet, because the dysfunctional immune responses limit the delayed type hypersensitivity responses which cause cavity formation in the lungs, HIV+ are more likely to be paucibacillary

For the studies, ART naive asymptomatic HIV+ patients (n=175) were recruited and examined for TB by smear and culture of sputum, blood and urine to confirm that these patients did not have TB. These patients represent the high-risk patients denoted by the blue circle in FIG. 2. These asymptomatic, non-TB HIV+ patients were bled and their serum stored at −80° C. The charts of these patients were examined repeatedly during the following months to identify patients who were subsequently diagnosed to have TB (pulmonary or extrapulmonary) and put on ATT by the clinician. Of the 175 asymptomatic HIV+ patients confirmed to have no evidence of TB, 34 died or were lost to follow up. Of the remaining 141 patients, 20 asymptomatic HIV+ patients progressed to TB during the course of follow up.

Sera obtained from 5 asymptomatic HIV+ patients who developed TB during follow up and were put on ATT were used to screen peptide microarrays bearing 15 aa peptides (overlapping by 7 aa) encompassing the entire sequence of the 4 proteins. Thus, there were a total of 158 peptides covering the entire amino acid sequence of the 4 proteins, in triplicate, on each array. Sera from patients with LTBI were used as controls. Diluted serum samples (1:50) were added onto the peptide microarray slide and the slides were incubated at 4° C. in a moist chamber overnight. The slides were washed with Tris buffered saline (TBS) with 0.05% Tween20 and then fluorescently labeled polyclonal goat anti-human IgG) was added. The slides were washed as before and dried. All the slides were scanned for fluorescence using GenePix 4000B microarray scanner (Axon Instruments) and the images were saved. Data was analyzed to identify the immunogenic peptides (IP).

Results were analysed to identify peptides that were recognized by antibodies in sera from asymptomatic HIV+ patients who later progressed to TB, but not antibodies in sera from patients with LTBI. Subjects with latent TB were used as negative controls. The goal was to identify peptides that are recognized by asymptomatic HIV+ patients who subsequently progressed to TB, and in HIV+ patients who are already progressed to TB. The foreground and background fluorescent intensities for all the peptide spots on a microarray slide was obtained from the Genepix result (gpr) files using Genepix software. The data was normalized in within- and across-experiment fashion. The normalized fluorescent intensities from the sera of LTBI subjects (who are HIV negative individuals) for each peptide was compared with asymptomatic HIV+ patients who subsequently progressed to TB, and HIV+ patients already progressed to TB using combination of approaches including Student T test, analysis of variance (ANOVA, p<0.1) and significance analysis of microarrays (SAM, false discovery rate or FDR set o<5%).

Results: Based on the cut-off defined above, 29/118 peptides on the microarrays were immunogenic; the remaining 89 peptides were negative at this cut-off. The following peptides (Table 2) were identified to be recognized by antibodies sera from in asymptomatic HIV+ patients who subsequently progressed to TB and were put on ATT, but not in subjects with LTBI.

TABLE 2

| Name | ID | T test | SEQ ID NO: |
|---|---|---|---|
| Rv1837c_0033 | DSFWAGVDKVVADLT | 0.0040 | 1 |
| Rv1837c_0121 | VLNARFALNAANARW | 0.0404 | 2 |
| Rv1837c_0225 | ESPTSVLLINHGLHI | 0.0132 | 3 |
| Rv1837c_0401 | HGPAEVAFTCELFSR | 0.0035 | 4 |
| Rv1837c_0409 | TCELFSRVEDVLGLP | 0.0534 | 5 |
| Rv1837c_0449 | AADRVVFINTGFLDR | 2.94E-05 | 6 |
| Rv1837c_0569 | GKRRATIEQLLTIPL | 0.0280 | 7 |
| Rv1837c_0593 | EIREEVDNNCQSILG | 0.0341 | 8 |
| Rv1837c_0649 | RHGVITSADVRASLE | 0.0755 | 9 |
| Rv1837c_0681 | PMAPNFDDSIAFLAA | 0.0281 | 10 |
| Rv1837c_0689 | SIAFLAAQELILSGA | 0.0110 | 11 |
| Rv3803c_0041 | VPSPSMGRDIPVAFL | 0.0388 | 12 |
| Rv3803c_0049 | DIPVAFLAGGPHAVY | 0.0401 | 13 |
| Rv3803c_0057 | GGPHAVYLLDAFNAG | 0.0640 | 14 |
| Rv3803c_0065 | LDAFNAGPDVSNWVT | 0.0319 | 15 |
| Rv3803c_0073 | DVSNWVTAGNAMNTL | 0.0449 | 16 |
| Rv3803c_0105 | YTNWEQDGSKQWDTF | 0.0029 | 17 |
| Rv3803c_0113 | SKQWDTFLSAELPDW | 0.0153 | 18 |
| Rv3803c_0121 | SAELPDWLAANRGLA | 0.0018 | 19 |
| Rv3803c_0273 | PASGDNGWGSWAPQL | 0.0521 | 20 |
| Rv3874_0017 | NFERISGDLKTQIDQ | 0.0732 | 21 |
| Rv3874_0033 | ESTAGSLQGQWRGAA | 0.0120 | 22 |
| Rv3874_0041 | GQWRGAAGTAAQAAV | 0.0184 | 23 |
| Rv3875_0001 | MTEQQWNFAGIEAAA | 0.0259 | 24 |
| Rv3875_0041 | AAWGGSGSEAYQGVQ | 0.0092 | 25 |
| Rv3875_0049 | EAYQGVQQKWDATAT | 0.0367 | 26 |

Similar arrays were also screened with sera from 6 HIV+TB+ patients. The peptides recognized by serum antibodies from these patients are listed in Table 3.

TABLE 3

| Name | ID | T test | SEQ ID NO: |
|---|---|---|---|
| Rv1837c_0121 | VLNARFALNAANARW | 0.0030 | 2 |
| Rv1837c_0185 | GSFGDATGFTVQDGQ | 0.0378 | 27 |
| Rv1837c_0225 | ESPTSVLLINHGLHI | 0.0226 | 3 |
| Rv1837c_0401 | HGPAEVAFTCELFSR | 0.0195 | 4 |
| Rv1837c_0409 | TCELFSRVEDVLGLP | 0.0159 | 5 |
| Rv1837c_0449 | AADRVVFINTGFLDR | 0.0278 | 6 |
| Rv1837c_0497 | VDAGLAAGFSGRAQV | 0.0692 | 28 |
| Rv1837c_0569 | GKRRATIEQLLTIPL | 0.0007 | 7 |
| Rv1837c_0593 | EIREEVDNNCQSILG | 0.0256 | 8 |
| Rv1837c_0649 | RHGVITSADVRASLE | 0.0118 | 9 |
| Rv1837c_0681 | PMAPNFDDSIAFLAA | 0.0164 | 10 |
| Rv1837c_0689 | SIAFLAAQELILSGA | 0.0011 | 11 |
| Rv3803c_0041 | VPSPSMGRDIPVAFL | 0.0416 | 12 |
| Rv3803c_0049 | DIPVAFLAGGPHAVY | 0.0225 | 13 |
| Rv3803c_0057 | GGPHAVYLLDAFNAG | 0.0499 | 14 |
| Rv3803c_0065 | LDAFNAGPDVSNWVT | 0.0137 | 15 |
| Rv3803c_0089 | GKGISVVAPAGGAYS | 0.0924 | 29 |
| Rv3803c_0105 | YTNWEQDGSKQWDTF | 0.0664 | 17 |
| Rv3803c_0113 | SKQWDTFLSAELPDW | 0.0875 | 18 |
| Rv3803c_0121 | SAELPDWLAANRGLA | 0.0692 | 19 |
| Rv3803c_0273 | PASGDNGWGSWAPQL | 0.0664 | 20 |
| Rv3874_0017 | NFERISGDLKTQIDQ | 0.0916 | 21 |
| Rv3875_0001 | MTEQQWNFAGIEAAA | 0.0032 | 24 |
| Rv3875_0041 | AAWGGSGSEAYQGVQ | 0.0324 | 25 |

A vast majority of the peptides recognized by antibodies in sera from asymptomatic HIV+ patients who progressed to TB, and HIV+TB+ patients were same. These peptides can therefore be the basis of a rapid screening test for routinely monitoring asymptomatic HIV+ patients and identifying asymptomatic HIV+ patients who have actively replicating bacteria and are at high risk for progression to TB.

The following peptides (Table 4) were non-immunogenic in the same assay:

TABLE 4

| Name | ID | T Test | SEQ ID NO: |
|---|---|---|---|
| Rv1837c_0001 | MTDRVSVGNLRIARV | 0.3370 | 30 |
| Rv1837c_0009 | NLRIARVLYDFVNNE | 0.7663 | 31 |
| Rv1837c_0025 | LPGTDIDPDSFWAGV | 0.1649 | 32 |
| Rv1837c_0041 | KVVADLTPQNQALLN | 0.8360 | 33 |
| Rv1837c_0057 | RDELQAQIDKWHRRR | 0.3734 | 34 |
| Rv1837c_0073 | IEPIDMDAYRQFLTE | 0.9880 | 35 |
| Rv1837c_0081 | YRQFLTEIGYLLPEP | 0.8858 | 36 |

TABLE 4-continued

| Name | ID | T Test | SEQ ID NO: |
|---|---|---|---|
| Rv1837c_0089 | GYLLPEPDDFTITTS | 0.1683 | 37 |
| Rv1837c_0097 | DFTITTSGVDAEITT | 0.4322 | 38 |
| Rv1837c_0113 | AGPQLVVPVLNARFA | 0.2809 | 39 |
| Rv1837c_0129 | NAANARWGSLYDALY | 0.1145 | 40 |
| Rv1837c_0137 | SLYDALYGTDVIPET | 0.3102 | 41 |
| Rv1837c_0145 | TDVIPETDGAEKGPT | 0.8194 | 42 |
| Rv1837c_0161 | NKVRGDKVIAYARKF | 0.3195 | 43 |
| Rv1837c_0169 | IAYARKFLDDSVPLS | 0.8664 | 44 |
| Rv1837c_0177 | DDSVPLSSGSFGDAT | 0.3701 | 45 |
| Rv1837c_0193 | FTVQDGQLVVALPDK | 0.6662 | 46 |
| Rv1837c_0201 | VVALPDKSTGLANPG | 0.1367 | 47 |
| Rv1837c_0209 | TGLANPGQFAGYTGA | 0.1371 | 48 |
| Rv1837c_0217 | FAGYTGAAESPTSVL | 0.4931 | 49 |
| Rv1837c_0233 | INHGLHIEILIDPES | 0.5401 | 50 |
| Rv1837c_0249 | VGTTDRAGVKDVILE | 0.8554 | 51 |
| Rv1837c_0257 | VKDVILESAITTIMD | 0.1450 | 52 |
| Rv1837c_0265 | AITTIMDFEDSVAAV | 0.2497 | 53 |
| Rv1837c_0273 | EDSVAAVDAADKVLG | 0.1098 | 54 |
| Rv1837c_0281 | AADKVLGYRNWLGLN | 0.6643 | 55 |
| Rv1837c_0289 | RNWLGLNKGDLAAAV | 0.2892 | 56 |
| Rv1837c_0297 | GDLAAAVDKDGTAFL | 0.1999 | 57 |
| Rv1837c_0305 | KDGTAFLRVLNRDRN | 0.4355 | 58 |
| Rv1837c_0321 | TAPGGGQFTLPGRSL | 0.1397 | 59 |
| Rv1837c_0329 | TLPGRSLMFVRNVGH | 0.8371 | 60 |
| Rv1837c_0337 | FVRNVGHLMTNDAIV | 0.1920 | 61 |
| Rv1837c_0345 | MTNDAIVDTDGSEVF | 0.1329 | 62 |
| Rv1837c_0353 | TDGSEVFEGIMDALF | 0.3233 | 63 |
| Rv1837c_0361 | GIMDALFTGLIAIHG | 0.2270 | 64 |
| Rv1837c_0369 | GLIAIHGLKASDVNG | 0.7169 | 65 |
| Rv1837c_0377 | KASDVNGPLINSRTG | 0.7954 | 66 |
| Rv1837c_0393 | IYIVKPKMHGPAEVA | 0.1256 | 67 |
| Rv1837c_0417 | EDVLGLPQNTMKIGI | 0.4912 | 68 |
| Rv1837c_0425 | NTMKIGIMDEERRTT | 0.9666 | 69 |
| Rv1837c_0457 | NTGFLDRTGDEIHTS | 0.1380 | 70 |
| Rv1837c_0465 | GDEIHTSMEAGPMVR | 0.1451 | 71 |
| Rv1837c_0481 | GTMKSQPWILAYEDH | 0.3758 | 72 |
| Rv1837c_0489 | ILAYEDHNVDAGLAA | 0.2791 | 73 |
| Rv1837c_0537 | ASTAWVPSPTAATLH | 0.5524 | 74 |
| Rv1837c_0545 | PTAATLHALHYHQVD | 0.1525 | 75 |
| Rv1837c_0553 | LHYHQVDVAAVQQGL | 0.2587 | 76 |
| Rv1837c_0561 | AAVQQGLAGKRRATI | 0.1045 | 77 |
| Rv1837c_0577 | QLLTIPLAKELAWAP | 0.2166 | 78 |
| Rv1837c_0585 | KELAWAPDEIREEVD | 0.6396 | 79 |
| Rv1837c_0601 | NCQSILGYVVRWVDQ | 0.3585 | 80 |
| Rv1837c_0641 | SQLLANWLRHGVITS | 0.8164 | 81 |
| Rv1837c_0665 | MAPLVDRQNAGDVAY | 0.1394 | 82 |
| Rv1837c_0697 | ELILSGAQQPNGYTE | 0.3844 | 83 |
| Rv1837c_0721 | FKARAAEKPAPSDRA | 0.9520 | 84 |
| Rv1837c_0727 | EKPAPSDRAGDDAAR | 0.1939 | 85 |
| Rv3803c_0001 | MKGRSALLRALWIAA | 0.8361 | 86 |
| Rv3803c_0017 | SFGLGGVAVAAEPTA | 0.1205 | 87 |
| Rv3803c_0033 | AAPYENLMVPSPSMG | 0.6467 | 88 |
| Rv3803c_0081 | GNAMNTLAGKGISVV | 0.3727 | 89 |
| Rv3803c_0097 | PAGGAYSMYTNWEQD | 0.2680 | 90 |
| Rv3803c_0129 | AANRGLAPGGHAAVG | 0.1181 | 91 |
| Rv3803c_0137 | GGHAAVGAAQGGYGA | 0.5380 | 92 |
| Rv3803c_0153 | ALAAFHPDRFGFAGS | 0.4459 | 93 |
| Rv3803c_0161 | RFGFAGSMSGFLYPS | 0.5373 | 94 |
| Rv3803c_0169 | SGFLYPSNTTTNGAI | 0.2065 | 95 |
| Rv3803c_0177 | TTTNGAIAAGMQQFG | 0.1217 | 96 |
| Rv3803c_0185 | AGMQQFGGVDTNGMW | 0.6299 | 97 |
| Rv3803c_0193 | VDTNGMWGAPQLGRW | 0.2561 | 98 |
| Rv3803c_0201 | APQLGRWKWHDPWVH | 0.8864 | 99 |
| Rv3803c_0209 | WHDPWVHASLLAQNN | 0.8575 | 100 |
| Rv3803c_0217 | SLLAQNNTRVWVWSP | 0.3332 | 101 |
| Rv3803c_0233 | NPGASDPAAMIGQAA | 0.3748 | 102 |
| Rv3803c_0249 | AMGNSRMFYNQYRSV | 0.5348 | 103 |
| Rv3803c_0257 | YNQYRSVGGHNGHFD | 0.4605 | 104 |
| Rv3803c_0281 | GSWAPQLGAMSGDIV | 0.1606 | 105 |
| Rv3803c_0285 | PQLGAMSGDIVGAIR | 0.4673 | 106 |
| Rv3874_0001 | MAEMKTDAATLAQEA | 0.9068 | 107 |
| Rv3874_0009 | ATLAQEAGNFERISG | 0.1957 | 108 |
| Rv3874_0025 | LKTQIDQVESTAGSL | 0.7063 | 109 |
| Rv3874_0049 | TAAQAAVVRFQEAAN | 0.4656 | 110 |
| Rv3874_065 | QKQELDEISTNIRQA | 0.4286 | 111 |
| Rv3874_0073 | STNIRQAGVQYSRAD | 0.3392 | 112 |
| Rv3874-0081 | VQYSRADEEQQQALS | 0.2712 | 113 |
| Rv3875_0009 | AGIEAAASAIQGNVT | 0.4223 | 114 |

TABLE 4-continued

| Name | ID | T Test | SEQ ID NO: |
|---|---|---|---|
| Rv3875_0017 | AIQGNVTSIHSLLDE | 0.3742 | 115 |
| Rv3875_0025 | IHSLLDEGKQSLTKL | 0.4326 | 116 |
| Rv3875_0057 | KWDATATELNNALQN | 0.2366 | 117 |
| Rv3875_0065 | LNNALQNLARTISEA | 0.7243 | 118 |

These studies have identified immunogenic epitopes of the 4 candidate proteins to which antibodies are present in sera from asymptomatic HIV+ patients who subsequently progressed to TB. These results also confirm that antibodies to these immunogenic epitopes will be detected during the progression of occult TB to clinical TB. Thus, using Ab responses that signal replication of in vivo bacteria, before the bacterial burden reaches the threshold of detection by any microbiological diagnostic techniques (microscopy, NAATs or culture) could potentially lead to a screening test that that can identify asymptomatic HIV+ patients who are likely to progress to TB. Such a test will have tremendous impact on TB-associated morbidity and mortality in this population.

While the invention has been described through specific examples, those skilled in the art will recognize that routine modifications can be made to the examples and embodiments. Such modifications are intended to be within the scope of this disclosure.

What is claimed is:

1. A method for early detection of active *M. tuberculosis* (Mtb) infection in an individual comprising: contacting a biological sample obtained from the individual with a peptide comprising the sequence as set forth in SEQ ID NOs 1-18, 20, or 27-29, wherein the peptide is 15-20 amino acids long; and detecting the formation of a complex of the peptide with antibodies present in the sample, wherein formation of the complex is an indication of active Mtb infection in the individual.

2. The method of claim 1, wherein the individual is HIV positive.

3. The method of claim 1, wherein the peptide of claim 1, is immobilized on a solid support.

4. The method of claim 1, wherein the individual does not show the presence of TB as assayed by direct sputum smear, concentrated sputum smear, nucleic acid amplification test, or bacterial culture.

5. The method of claim 1, wherein the biological sample is blood, serum, plasma, urine, pleural fluid, ocular fluid or saliva.

6. A method for predicting risk of an asymptomatic immunocompromised individual developing active tuberculosis (TB) comprising:

a) contacting a biological sample obtained from the individual with a peptide comprising the sequence as set forth in SEQ ID NOs 1 18, 20, or 27-29, wherein the peptide is 15-20 amino acids long;

b) detecting the presence of a complex formed of the peptide with the an antibody in the sample, wherein the antibody is specific for an Mtb antigen selected from the group consisting of malate synthase (MS), MPT51, ESAT6 and CFP10;

c) comparing the level of complexes in the sample to the level of complexes in a control; and d) identifying the individual to be at risk of developing active TB if the level of complexes in the sample from the individual is more than the level of complexes in the control.

7. The method of claim 6, wherein the individual is HIV positive.

8. The method of claim 6, wherein the control is a peptide having a sequence of any one of SEQ ID NOs 30-118.

9. The method of claim 6, wherein the presence of the complex is detected by using a detectably labeled second antibody that is specific for the antibody in the sample.

10. The method of claim 6, wherein the individual does not show the presence of TB as assayed by direct sputum smear, concentrated sputum smear, nucleic acid amplification test, or bacterial culture.

11. The method of claim 6, wherein the biological sample is blood, serum, plasma, urine, pleural fluid, ocular fluid or saliva.

12. A method of monitoring the progression toward active tuberculosis (TB) in an immunocompromised individual comprising:
   a) contacting each of at least two biological samples obtained from the individual at two different times with a peptide comprising the sequence as set forth in SEQ ID NOs 1 18, 20, or 27-29, wherein the peptide is 15-20 amino acids long;
   b) detecting the formation of a complex of the peptide with an antibody present in the sample, wherein the antibody is specific for malate synthase (MS), MPT51, ESAT6, or CFP10;
   c) comparing the level of the complexes in the two samples; and
   d) if the level of the complexes is more in the sample obtained at the later time, identifying the individual as progressing toward active TB.

13. The method of claim 12, wherein the individual is HIV positive.

14. The method of claim 12, wherein the presence of the complex is detected by using a detectably labeled second antibody that is specific for the antibody in the sample.

15. The method of claim 12, wherein the biological sample is blood, serum, plasma, urine, pleural fluid, ocular fluid or saliva.

16. The method of claim 1, wherein the peptide is 15 amino acids long.

17. The method of claim 6, wherein the peptide is 15 amino acids long.

18. The method of claim 12, wherein the peptide is 15 amino acids long.

* * * * *

UNITED STATES PATENT AND TRADEMARK OFFICE
CERTIFICATE OF CORRECTION

PATENT NO. : 10,883,989 B2
APPLICATION NO. : 15/564086
DATED : January 5, 2021
INVENTOR(S) : Laal Page 1 of 1

It is certified that error appears in the above-identified patent and that said Letters Patent is hereby corrected as shown below:

In the Claims

Column 54, Line 58, in Claim 6, "SEQ ID NOs 1 18, 20, or 27-29" should read:
--SEQ ID NOs 1-18, 20, or 27-29--;

Column 54, Line 61, in Claim 6, "peptide with the an antibody in the sample" should read:
--peptide with an antibody in the sample--;

Column 55, Lines 24-25, in Claim 12, "SEQ ID NOs 1 18, 20, or 27-29" should read:
--SEQ ID NOs 1-18, 20, or 27-29--.

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*